United States Patent
Ray, II

(10) Patent No.: US 9,962,391 B2
(45) Date of Patent: *May 8, 2018

(54) COMPOSITION AND METHOD FOR COMPOUNDED THERAPY

(71) Applicant: CMPD LICENSING, LLC, Conroe, TX (US)

(72) Inventor: Jay Richard Ray, II, Conroe, TX (US)

(73) Assignee: CMPD LICENSING, LLC, Conroe, TX (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/354,348

(22) Filed: Nov. 17, 2016

(65) Prior Publication Data
US 2017/0136028 A1    May 18, 2017

Related U.S. Application Data

(63) Continuation-in-part of application No. 14/996,560, filed on Jan. 15, 2016, which is a continuation-in-part of application No. 13/448,088, filed on Apr. 16, 2012, now Pat. No. 9,468,599, which is a continuation-in-part of application No. 13/409,738, filed on Mar. 1, 2012, now abandoned, which is a continuation of application No. 13/337,598, filed on Dec. 27, 2011, now abandoned.

(51) Int. Cl.
| | |
|---|---|
| *A61K 31/5415* | (2006.01) |
| *A61K 9/00* | (2006.01) |
| *A61K 31/195* | (2006.01) |
| *A61K 31/167* | (2006.01) |
| *A61K 9/107* | (2006.01) |
| *A61K 9/06* | (2006.01) |
| *A61K 31/196* | (2006.01) |
| *A61K 31/53* | (2006.01) |
| *A61K 31/7048* | (2006.01) |

(52) U.S. Cl.
CPC ........ *A61K 31/5415* (2013.01); *A61K 9/0014* (2013.01); *A61K 9/06* (2013.01); *A61K 9/107* (2013.01); *A61K 31/167* (2013.01); *A61K 31/195* (2013.01); *A61K 31/196* (2013.01); *A61K 31/53* (2013.01); *A61K 31/7048* (2013.01)

(58) Field of Classification Search
CPC ...... A61K 31/54; A61K 31/495; A61K 31/50; A61K 31/135
USPC ..................... 514/226.5, 248, 648
See application file for complete search history.

(56) References Cited

U.S. PATENT DOCUMENTS

| | | | |
|---|---|---|---|
| 3,711,602 A | 1/1973 | Herschler | |
| 4,562,060 A | 12/1985 | Broberg et al. | |
| 4,937,078 A | 6/1990 | Broberg et al. | |
| 5,993,836 A | 11/1999 | Castillo | |
| 6,248,789 B1 | 6/2001 | Weg | |
| 6,290,986 B1 | 9/2001 | Murdock et al. | |
| 6,299,902 B1 | 10/2001 | Jun et al. | |
| 6,410,062 B1 | 6/2002 | Callaghan et al. | |
| 7,166,641 B2 | 1/2007 | Lee et al. | |
| 8,535,738 B2 | 9/2013 | Collins et al. | |
| 2001/0029257 A1 | 10/2001 | Murdock et al. | |
| 2003/0124176 A1 | 7/2003 | Hsu et al. | |
| 2004/0101582 A1 | 5/2004 | Wolicki | |
| 2004/0208914 A1 | 10/2004 | Richlin | |
| 2004/0265364 A1* | 12/2004 | Ozturk ................. | A61K 31/195 424/449 |
| 2005/0038062 A1 | 2/2005 | Burns et al. | |
| 2005/0187212 A1* | 8/2005 | Ohki .................... | A61K 9/7053 514/226.5 |
| 2006/0140986 A1 | 6/2006 | Fita | |
| 2006/0223788 A1 | 10/2006 | Cathcart | |
| 2007/0065463 A1 | 3/2007 | Aung-Din | |
| 2007/0093420 A1 | 4/2007 | Yeomans et al. | |
| 2007/0116730 A1 | 5/2007 | Simmons et al. | |
| 2007/0269393 A1 | 11/2007 | Wepfer | |
| 2007/0269465 A9 | 11/2007 | Fita | |
| 2008/0233183 A1 | 9/2008 | McCook et al. | |
| 2009/0162421 A1 | 6/2009 | Geisslinger et al. | |
| 2010/0016436 A1 | 1/2010 | Staniforth et al. | |
| 2010/0080797 A1 | 4/2010 | Yeomans et al. | |
| 2010/0160299 A1 | 6/2010 | Baker et al. | |

(Continued)

FOREIGN PATENT DOCUMENTS

| | | |
|---|---|---|
| EP | 0964552 | 8/2009 |
| IN | 373/MUM/2005 | 3/2007 |

(Continued)

OTHER PUBLICATIONS

Pain Management Compounding, (Published 2010).*

(Continued)

*Primary Examiner* — Timothy P Thomas
*Assistant Examiner* — George W Kosturko
(74) *Attorney, Agent, or Firm* — Akerman LLP

(57) ABSTRACT

A method of compounding a transdermal cream may include grinding one or more tablets of a Non-Steroidal Anti-Inflammatory Drug (NSAID) and one or more nerve depressants, anticonvulsants, or combinations thereof to produce a fine powder. The find powder may be wetted and added to an eutectic mixture of lidocaine and prilocaine in an emulsified topical cream in the form of a lidocaine 2.5%-prilocaine 2.5% cream. The compounded transdermal may include between 0.05% and 0.15% by weight meloxicam, between 1.0% and 5.0% by weight gabapentin, and at least 80% by weight of the lidocaine 2.5%-prilocaine 2.5% cream.

8 Claims, 15 Drawing Sheets

(56) References Cited

U.S. PATENT DOCUMENTS

| | | |
|---|---|---|
| 2010/0184817 A1 | 7/2010 | Wolicki |
| 2010/0221309 A1 | 9/2010 | Myers et al. |
| 2010/0226972 A1 | 9/2010 | Lutz |
| 2010/0286205 A1 | 11/2010 | McCarron et al. |
| 2010/0287884 A1 | 11/2010 | Sheshadri et al. |
| 2011/0015229 A1 | 1/2011 | Zhang et al. |
| 2011/0028460 A1 | 2/2011 | Kisak et al. |
| 2011/0033545 A1 | 2/2011 | Wang |
| 2011/0250212 A1 | 10/2011 | Yeomans et al. |
| 2011/0257257 A1 | 10/2011 | Shapira et al. |
| 2013/0085171 A1 | 4/2013 | Ray |
| 2013/0165429 A1 | 6/2013 | Ray et al. |
| 2013/0165430 A1 | 6/2013 | Ray et al. |
| 2015/0148305 A1 | 5/2015 | Ray et al. |
| 2015/0359740 A1 | 12/2015 | Ray |
| 2015/0359767 A1 | 12/2015 | Ray |
| 2015/0359768 A1 | 12/2015 | Ray |

FOREIGN PATENT DOCUMENTS

| | | |
|---|---|---|
| JP | 7309749 | 11/1995 |
| WO | 2004/110423 | 12/2004 |
| WO | 2013/048453 | 4/2013 |
| WO | 2013/101949 | 7/2013 |

OTHER PUBLICATIONS

Furst et al (Semin Arthritis Rheum. vol. 26 (6 Suppl. 1) Published 1997. Abstract provided).*
Erickson et al., (Pharmacy Times, published online Jan. 1, 2005).*
Gennaro, R. et al., Remington: Practice of the Science and Pharmacy. 19th Edition. Published 1995. pp. 1515-1517.*
Gabapentin (Drugs.com). Published 2004.*
(B and B Pharmacy Compounding Published 2010) (Year: 2010).*
Non-Final Office Action dated Feb. 9, 2016 for U.S. Appl. No. 14/836,455, filed Aug. 26, 2015 (Inventor: Jay Richard Ray II ) (8 pages).
Response to Restriction Requirement filed Jan. 7, 2016 for U.S. Appl. No. 14/836,455, filed Aug. 26, 2015 (Inventor: Jay Richard Ray II ) (2 pages).
Restriction Requirement dated Dec. 10, 2015 for U.S. Appl. No. 14/836,455, filed Aug. 26, 2015 (Inventor: Jay Richard Ray II ) (6 pages).
Restriction Requirement dated Jan. 29, 2016 for U.S. Appl. No. 14/836,491, filed Aug. 26, 2015 (Inventor: Jay Richard Ray II ) (6 pages).
Response to Restriction Requirement filed Mar. 4, 2016 for U.S. Appl. No. 14/836,509, filed Aug. 26, 2015 (published as WO 2013/101949) (Inventor: Jay Richard Ray II) (8 pages).
Restriction Requirement dated Jan. 6, 2016 for U.S. Appl. No. 14/836,509, filed Aug. 26, 2015 (published as WO 2013/101949) (Inventor: Jay Richard Ray II ) (7 pages).
International Search Report dated Mar. 5, 2013 for International Patent Application No. PCT/US12/71846 filed Dec. 27, 2012 (published as WO 2013/101949) (Applicant: JCDS Holdings, LLC) (4 pages).
Written Opinion dated Mar. 5, 2013 for International Patent Application No. PCT/US12/71846 filed Dec. 27, 2012 (published as WO 2013/101949) (Applicant: JCDS Holdings, LLC) (7 pages).
International Preliminary Report on Patentability dated May 5, 2015 for International Patent Application No. PCT/US12/71846 filed Dec. 27, 2012 (published as WO 2013/101949) (Applicant: JCDS Holdings, LLC) (7 pages).
International Search Report dated Feb. 23, 2012 for International Patent Application No. PCT/US2011/054324 filed Sep. 30, 2011 (published as WO 2013/048453) (Applicant: Jay Richard Ray, II) (3 pages).
Written Opinion dated Feb. 23, 2012 for International Patent Application No. PCT/US2011/054324 filed Sep. 30, 2011 published as WO 2013/048453) (Applicant: Jay Richard Ray, II) (6 pages).
International Preliminary Report on Patentability dated Apr. 1, 2014 for International Patent Application No. PCT/US2011/054324 filed Sep. 30, 2011 (published as WO 2013/048453) (Applicant: Jay Richard Ray, II) (7 pages).
Restriction Requirement dated Jul. 18, 2012 for U.S. Appl. No. 13/328,369, filed Dec. 16, 2011 (Inventor: Jay Richard Ray II) (6 pages).
Response to Restriction Requirement dated Aug. 2, 2012 for U.S. Appl. No. 13/328,369, filed Dec. 16, 2011 (Inventor: Jay Richard Ray II) (2 pages).
Non-Final Office Action dated Oct. 4, 2012 for U.S. Appl. No. 13/328,369, filed Dec. 16, 2011 (Inventor: Jay Richard Ray II) (7 pages).
Response filed Dec. 18, 2012 for U.S. Appl. No. 13/328,369, filed Dec. 16, 2011 (Inventor: Jay Richard Ray II) (11 pages).
Final Office Action dated Jan. 14, 2013 for U.S. Appl. No. 13/328,369, filed Dec. 16, 2011 (Inventor: Jay Richard Ray II) (10 pages).
Response filed Mar. 22, 2013 for U.S. Appl. No. 13/328,369, filed Dec. 16, 2011 (Inventor: Jay Richard Ray II) (11 pages).
Non-Final Office Action dated Feb. 5, 2014 for U.S. Appl. No. 13/328,369, filed Dec. 16, 2011 (Inventor: Jay Richard Ray II) (10 pages).
Response dated Jul. 7, 2014 for U.S. Appl. No. 13/328,369, filed Dec. 16, 2011 (Inventor: Jay Richard Ray II) (15 pages).
Final Office Action dated Oct. 6, 2014 for U.S. Appl. No. 13/328,369, filed Dec. 16, 2011 (Inventor: Jay Richard Ray I) (10 pages).
Examiner Interview Summary dated Dec. 2, 2014 for U.S. Appl. No. 13/328,369, filed Dec. 16, 2011 (Inventor: Jay Richard Ray II) (2 pages).
Notice of Appeal filed Feb. 6, 2015 for U.S. Appl. No. 13/328,369, filed Dec. 16, 2011 (Inventor: Jay Richard Ray II) (1 page).
Response filed Apr. 3, 2015 for U.S. Appl. No. 13/328,369, filed Dec. 16, 2011 (Inventor: Jay Richard Ray II) (10 pages).
Appeal Brief filed Apr. 6, 2015 for U.S. Appl. No. 13/328,369, filed Dec. 16, 2011 (Inventor: Jay Richard Ray II) (30 pages).
Advisory Action dated Apr. 17, 2015 for U.S. Appl. No. 13/328,369, filed Dec. 16, 2011 (Inventor: Jay Richard Ray II) (3 pages).
Examiner's Answer dated Sep. 16, 2015 for U.S. Appl. No. 13/328,369, filed Dec. 16, 2011 (Inventor: Jay Richard Ray II) (9 pages).
Reply Brief filed Oct. 29, 2015 for U.S. Appl. No. 13/328,369, filed Dec. 16, 2011 (Inventor: Jay Richard Ray II) (10 pages).
Docketing Notice issued Nov. 17, 2015 for U.S. Appl. No. 13/328,369, filed Dec. 16, 2011 (Inventor: Jay Richard Ray II) (2 pages).
Nayak et al., (2006) Evaluation of three topical anaesthetic agents against pain: a clinical study. Indian J Dent Res. 17(4):155-160.
Okon, (2007) Ketamine: an introduction for the pain and palliative medicine physician. Pain Physician. 10(3):493-500.
Oskouee, et al., (2007) Bandage contact lens and topical indomethacin for treating persistent corneal epithelial defects after vitreoretinal surgery. Cornea. 26(10):1178-1181.
Park et al., (2005) Transdermal delivery of piroxicam using microemulsions. Arch Pharm Res. 28(2):243-248. (Abstract Only).
Patel et al., (1996) Comparison of ketoprofen, piroxicam, and diclofenac gels in the treatment of acute soft-tissue injury in general practice. General Practice Study Group. Clin Ther. 18(3):497-507.
PCCA (Fall 2011) T3 Sodium Dilution (1:1000). Issue 1, p. 35.
Pelfini et al., (1989) Flurbiprofen in gel: study of acceptability, tolerability and evaluation of its allergenic potential. G Ital Dermatol Venereol. 124(9):XLIII-XLVI.
Peniston et al., (2012) Long-term tolerability of topical diclofenac sodium 1% gel for osteoarthritis in seniors and patients with comorbidities. Clin Interv Aging. 7:517-523.
Pénzes et al., (2005) Topical absorption of piroxicam from organogels—in vitro and in vivo correlations. Int J Pharm. 298(1):47-54.
Pharmacy Onesource. Simplifi 797—USP Chapter 797 Compliance Management (2 pages), Available at http://www.pharmacyonesource.com/simplifi797/.

(56) References Cited

OTHER PUBLICATIONS

Picazo et al., (2006) Examination of the interaction between peripheral diclofenac and gabapentin on the 5% formalin test in rats. Life Sci. 79(24):2283-2287.

Poterucha et al., (2013) Topical amitriptyline combined with ketamine for the treatment of erythromelalgia: a retrospective study of 36 patients at Mayo Clinic. J Drugs Dermatol. 12(3):308-310.

Pöyhiä et al., (2006) Topically administered ketamine reduces capsaicin-evoked mechanical hyperalgesia. Clin J Pain. 22(1):32-36.

Predel et al., (2012) Efficacy and safety of diclofenac diethylamine 2.32% gel in acute ankle sprain. Med Sci Sports Exerc. 44(9):1629-1636.

Predel et al., (2013) A randomized, double-blind, placebo-controlled multicentre study to evaluate the efficacy and safety of diclofenac 4% spray gel in the treatment of acute uncomplicated ankle sprain. J Int Med Res. 41(4):1187-1202.

Prommer, (2009) Topical analgesic combinations for bortezomib neuropathy. J Pain Symptom Manage. 37(3):e3-5.

Rahimi et al., (2012) Comparison of topical anesthetic cream (EMLA) and diclofenac suppository for pain relief after hemorrhoidectomy: a randomized clinical trial. Surg Today. 42(12):1201-1205.

Rao et al., (2008) Efficacy of lamotrigine in the management of chemotherapy-induced peripheral neuropathy: a phase 3 randomized, double-blind, placebo-controlled trial, N01C3. Cancer. 112(12):2802-2808.

Rashwana et al., (2014) Effect of tramadol gargle on postoperative sore throat: A double blinded randomized placebo controlled study. Egyptian J Anaesthesia. 30(3): 235-239.

Renno et al., (2006) The efficacy of lamotrigine in the management of chemotherapy-induced peripheral neuropathy: A phase III randomized, double blind, placebo-controlled NCCTG trial, N01C3. J Clin Oncol. 24(18S):530. (Abstract Only).

Ritchie, (1996) A clinical evaluation of flurbiprofen LAT and piroxicam gel: a multicentre study in general practice. Clin Rheumatol. 15(3):243-247. (Abstract Only).

Roth et al., (2014) Efficacy and safety of a topical diclofenac solution (pennsaid) in the treatment of primary osteoarthritis of the knee: a randomized, double-blind, vehicle-controlled clinical trial. Arch Intern Med. 164 (18):2017-2023.

Rother et al., (2013) A randomized, double-blind, phase III trial in moderate osteoarthritis knee pain comparing topical ketoprofen gel with ketoprofen-free gel. J Rheumatol. 40(10):1742-1748.

Rovenský et al., (2001) Treatment of knee osteoarthritis with a topical non-steroidal antiinflammatory drug. Results of a randomized, double-blind, placebo-controlled study on the efficacy and safety of a 5% ibuprofen cream. Drugs Exp Clin Res. 27(5-6):209-221.

Rowbotham et al., (1995) Topical lidocaine gel relieves postherpetic neuralgia. Ann Neurol. 37(2):246-253. (Abstract Only).

Russell, (1991) Piroxicam 0.5% topical gel compared to placebo in the treatment of acute soft tissue injuries: a double-blind study comparing efficacy and safety. Clin Invest Med 14(1):35-43. (Abstract Only).

Sakai et al., (2004) Quantitative and selective evaluation of differential sensory nerve block after transdermal lidocaine. Anesth Analg. 98(1):248-251.

Samson et al., (2007) Eutectic mixture of local anesthetic (EMLA) decreases pain during humeral block placement in nonsedated patients. Anesth Analg. 105(2):512-515.

Sanabria et al., (2013) Ocular pain after intravitreal injection. Curr Eye Res. 38(2):278-282.

Sandroni et al., (2006) Combination gel of 1% amitriptyline and 0.5% ketamine to treat refractory erythromelalgia pain: a new treatment option? Arch Dermatol. 142(3):283-286. (Abstract Only).

Sanosil, (2010) Sanosil Product Description Sheet. (7 pages).

Sawynok et al., (1999) Peripheral antinociceptive actions of desipramine and fluoxetine in an inflammatory and neuropathic pain test in the rat. Pain. 82(2):149-158. (Abstract Only).

Scott et al., (1999) Use of transdermal amitriptyline gel in a patient with chronic pain and depression. Pharmacotherapy. 19(2):236-239. (Abstract Only).

Segatto et al., (2013) Comparative study of actinic keratosis treatment with 3% diclofenac sodium and 5% 5-fluorouracil. An Bras Dermatol. 88(5):732-738.

Shimoda et al., (1993) Transdermal application of 10% lidocaine-gel for management of pain associated with herpes zoster. Masui. 42(8):1171-1176. (Abstract Only).

Sick Kids Pharmacy Order Form for Baclofen (5 mg/mL Oral Suspension) (Apr. 2007) (1 page).

Simon et al., (2009) Efficacy and safety of topical diclofenac containing dimethyl sulfoxide (DMSO) compared with those of topical placebo, DMSO vehicle and oral diclofenac for knee osteoarthritis. Pain. 143(3):238-245.

Slatkin et al., (2003) Topical ketamine in the treatment of mucositis pain. Pain Med. 4(3):298-303.

Suresh et al., (2001) Intracrevicular application of 03% Flurbiprofen gel and 0.3% Triclosan gel as anti inflammatory agent. A comparative clinical study. Indian J Dent Res. 12(2):105-112. (Abstract Only).

Taddio et al., (2002) Lidocaine-prilocaine cream versus tetracaine gel for procedural pain in children. Ann Pharmacother. 36(4):687-692. (Abstract Only).

Tekelioglu et al., (2013) Comparison of topical tramadol and ketamine in pain treatment after tonsillectomy. Paediatr Anaesth. 23(6):496-501.

Thaller et al., (2000) The effect of pre-operative topical flurbiprofen or diclofenac on pupil dilatation. Eye (Lond). 14 ( Pt 4):642-645.

Tham et al., (1994) An assessment of prilocaine as a topical anaesthetic agent for fibreoptic bronchoscopy in comparison with lidocaine. Acta Anaesthesiol Scand. 38(5):442-447.

Tiso et al., (2010) Oral versus topical Ibuprofen for chronic knee pain: a prospective randomized pilot study. Pain Physician. 13(5):457-467.

Titlic et al., (2008) Lamotrigine in the treatment of pain syndromes and neuropathic pain. Bratisl Lek Listy. 109 (9):421-424. (Abstract Only).

Toker et al., (2006) The effects of topical ketorolac and indomethacin on measles conjunctivitis: randomized controlled trial. Am J Ophthalmol. 141(5):902-905.

Trnavský et al., (2004) Efficacy and safety of 5% ibuprofen cream treatment in knee osteoarthritis. Results of a randomized, double-blind, placebo-controlled study. J Rheumatol. 31(3):565-572.

Underwood et al., (2008) Topical or oral ibuprofen for chronic knee pain in older people. The TOIB study. Health Technol Assess 12(22):iii-iv, ix-155.

United States Pharmacopeial Convention, (2008) No. 1231—Water for Pharmaceutical Purposes (50 pages).

United States Pharmacopeial Convention, (2013) Official Monograph for Lidocaine and Prilocaine Cream. USP 36: 4115-4117. (3 pages).

United States Pharmacopeial Convention, (2013) Official Monograph for Meloxicam Tablets. USP 36: 4230-4231. (2 pages).

United States Pharmacopeial Convention, (2013) Official Monograph for Topiramate. USP 36: 5431-5434. (4 pages).

Vadivelu et al., (2010) Recent advances in postoperative pain management. Yale J Biol Med. 83(1):11-25.

Vranken, (2009) Mechanisms and treatment of neuropathic pain. Cent Nerv Syst Agents Med Chem. 9(1):71-78. (Abstract Only).

Whitefield et al., (2002) Comparative efficacy of a proprietary topical ibuprofen gel and oral ibuprofen in acute soft tissue injuries: a randomized, double-blind study. J Clin Pharm Ther. 27(6):409-417.

Wiffen et al., (2007) Lamotrigine for acute and chronic pain. Cochrane Database Syst Rev. (2):CD006044. (Abstract Only).

Wiffen et al., (2011) Lamotrigine for acute and chronic pain. Cochrane Database Syst Rev. (2):CD006044. Update in Wiffen PJ, et al. (2013) Lamotrigine for chronic neuropathic pain and fibromyalgia in adults. Cochrane Database Syst Rev. 12:CD006044.

Wiffen et al., (2013) Topiramate for neuropathic pain and fibromyalgia in adults. Cochrane Database Syst Rev. 8: CD008314.

(56) References Cited

OTHER PUBLICATIONS

Wyllie et al., (2012) The role of local anaesthetics in premature ejaculation. BJU Int. 110(11 Pt C):E943-E948.
Yavas et al., (2007) Preoperative topical indomethacin to prevent pseudophakic cystoid macular edema. J Cataract Refract Surg. 33(5):804-807.
Yeoh et al., (2012) Pain during venous cannulation: Double-blind, randomized clinical trial of analgesic effect between topical amethocaine and eutectic mixture of local anesthetic. J Anaesthesiol Clin Pharmacol. 28(2):205-209.
Zacher et al., (2008) Topical diclofenac and its role in pain and inflammation: an evidence-based review. Curr Med Res Opin. 24(4):925-950. (Abstract Only).
Notice of Abandonment dated Mar. 28, 2013 for U.S. Appl. No. 13/337,598, filed Dec. 27, 2011 (Inventor: Jay Richard Ray II) (2 pages).
Express Abandonment to Obtain a Refund filed Mar. 22, 2013 for U.S. Appl. No. 13/337,598, filed Dec. 27, 2011 (Inventor: Jay Richard Ray II) (1 page).
Decision on Petition issued Nov. 14, 2012 for U.S. Appl. No. 13/337,598, filed Dec. 27, 2011 (Inventor: Jay Richard Ray II) (1 page).
Petition for Express Abandonment to Obtain a Refund filed Nov. 6, 2012 for U.S. Appl. No. 13/337,598, filed Dec. 27, 2011 (Inventor: Jay Richard Ray II) (1 page).
Restriction Requirement dated Nov. 2, 2012 for U.S. Appl. No. 13/337,598, filed Dec. 27, 2011 (Inventor: Jay Richard Ray II) (9 pages).
Notice of Abandonment dated Aug. 6, 2012 for U.S. Appl. No. 13/409,738, filed Mar. 1, 2012 (Inventor: Jay Richard Ray II) (2 pages).
Decision on Petition issued Aug. 6, 2012 for U.S. Appl. No. 13/409,738, filed Mar. 1, 2012 (Inventor: Jay Richard Ray II) (1 page).
Petition for Express Abandonment to Obtain a Refund filed Aug. 1, 2012 for U.S. Appl. No. 13/409,738, filed Mar. 1, 2012 (Inventor: Jay Richard Ray II) (1 page).
Non-Final Office Action dated Nov. 27, 2015 for U.S. Appl. No. 13/448,088, filed Apr. 16, 2012 (Inventor: Jay Richard Ray II) (19 pages).
Response filed Aug. 6, 2015 for U.S. Appl. No. 13/448,088, filed Apr. 16, 2012 (Inventor: Jay Richard Ray II) (20 pages).
Non-Final Office Action dated Apr. 7, 2015 for U.S. Appl. No. 13/448,088, filed Apr. 16, 2012 (Inventor: Jay Richard Ray II) (21 pages).
Response filed May 27, 2014 for U.S. Appl. No. 13/448,088, filed Apr. 16, 2012 (Inventor: Jay Richard Ray II) (12 pages).
Final Office Action dated Feb. 25, 2014 for U.S. Appl. No. 13/448,088, filed Apr. 16, 2012 (Inventor: Jay Richard Ray II) (13 pages).
Response filed Nov. 4, 2013 for U.S. Appl. No. 13/448,088, filed Apr. 16, 2012 (Inventor: Jay Richard Ray II) (12 pages).
Non-Final Office Action dated May 2, 2013 for U.S. Appl. No. 13/448,088, filed Apr. 16, 2012 (Inventor: Jay Richard Ray II) (14 pages).
Response filed Mar. 4, 2013 for U.S. Appl. No. 13/448,088, filed Apr. 16, 2012 (Inventor: Jay Richard Ray II) (13 pages).
Non-Final Office Action dated Dec. 31, 2012 for U.S. Appl. No. 13/448,088, filed Apr. 16, 2012 (Inventor: Jay Richard Ray II) (10 pages).
Response to Restriction Requirement dated Oct. 26, 2012 for U.S. Appl. No. 13/448,088, filed Apr. 16, 2012 (Inventor: Jay Richard Ray II) (9 pages).
Restriction Requirement dated Sep. 26, 2012 for U.S. Appl. No. 13/448,088, filed Apr. 16, 2012 (Inventor: Jay Richard Ray II) (6 pages).
Non-Final Office Action dated Mar. 4, 2016 for U.S. Appl. No. 13/564,525, filed Aug. 1, 2012 (Inventor: Jay Richard Ray II) (22 pages).
Advisory Action with AFCP 2.0 Decision dated Jul. 27, 2015 for U.S. Appl. No. 13/564,525, filed Aug. 1, 2012 (Inventor: Jay Richard Ray II) (4 pages).
Response with AFCP 2.0 Request dated Jul. 17, 2015 for U.S. Appl. No. 13/564,525, filed Aug. 1, 2012 (Inventor: Jay Richard Ray II) (11 pages).
Final Office Action dated Jun. 9, 2015 for U.S. Appl. No. 13/564,525, filed Aug. 1, 2012 (Inventor: Jay Richard Ray II) (18 pages).
Response dated May 12, 2015 for U.S. Appl. No. 13/564,525, filed Aug. 1, 2012 (Inventor: Jay Richard Ray II) (10 pages).
Non-Final Office Action dated Feb. 12, 2015 for U.S. Appl. No. 13/564,525, filed Aug. 1, 2012 (Inventor: Jay Richard Ray II) (12 pages).
Terminal Disclaimer filed Sep. 26, 2014 and Approval for U.S. Appl. No. 13/564,525, filed Aug. 1, 2012 (Inventor: Jay Richard Ray II) (3 pages).
Response dated Nov. 4, 2013 for U.S. Appl. No. 13/564,525, filed Aug. 1, 2012 (Inventor: Jay Richard Ray II) (10 pages).
Terminal Disclaimer filed Sep. 30, 2013 and Disapproval for U.S. Appl. No. 13/564,525, filed Aug. 1, 2012 (Inventor: Jay Richard Ray II) (3 pages).
Final Office Action dated May 23, 2013 for U.S. Appl. No. 13/564,525, filed Aug. 1, 2012 (Inventor: Jay Richard Ray II) (19 pages).
Response filed Apr. 16, 2013 for U.S. Appl. No. 13/564,525, filed Aug. 1, 2012 (Inventor: Jay Richard Ray II) (14 pages).
Non-Final Office Action issued Jan. 18, 2013 for U.S. Appl. No. 13/564,525, filed Aug. 1, 2012 (Inventor: Jay Richard Ray II) (14 pages).
Response to Restriction Requirement dated Dec. 3, 2012 for U.S. Appl. No. 13/564,525, filed Aug. 1, 2012 (Inventor: Jay Richard Ray II) (9 pages).
Restriction Requirement dated Nov. 2, 2012 for U.S. Appl. No. 13/564,525, filed Aug. 1, 2012 (Inventor: Jay Richard Ray II) (9 pages).
Response dated Nov. 24, 2015 for U.S. Appl. No. 14/609,063, filed Nov. 14, 2015 (Inventor: Jay Richard Ray II) (20 pages).
Non-Final Office Action dated Aug. 27, 2015 for U.S. Appl. No. 14/609,063, filed Nov. 14, 2015 (Inventor: Jay Richard Ray II) (15 pages).
Response to Restriction Requirement dated Jun. 4, 2015 for U.S. Appl. No. 14/609,063, filed Nov. 14, 2015 (Inventor: Jay Richard Ray II ) (9 pages).
Restriction Requirement dated May 13, 2015 for U.S. Appl. No. 14/609,063, filed Nov. 14, 2015 (Inventor: Jay Richard Ray II) (5 pages).
Preliminary Amendment dated Feb. 19, 2015 for U.S. Appl. No. 14/609,063, filed Nov. 14, 2015 (Inventor: Jay Richard Ray II) (9 pages).
Airaksinen et al., (1993) Ketoprofen 2.5% gel versus placebo gel in the treatment of acute soft tissue injuries. Int J Clin Pharmacol Ther Toxicol. 31(11):561-563. (Abstract Only).
Akarsu et al., (2011) Comparison of topical 3% diclofenac sodium gel and 5% imiquimod cream for the treatment of actinic keratoses. Clin Exp Dermatol. 36(5):479-484.
Akbay et al., (2010). Analgesic efficacy of topical tramadol in the control of postoperative pain in children after tonsillectomy. J Anesth. 24(5):705-708.
Akermark et al., (1990) Topical indomethacin in overuse injuries in athletes. A randomized double-blind study comparing Elmetacin with oral indomethacin and placebo. Int J Sports Med. 11(5):393-396.
Akinturk et al., (2007) Effect of piroxicam gel for pain control and inflammation in Nd:YAG 1064-nm laser hair removal. J Eur Acad Dermatol Venereol. 21(3):380-383. (Abstract Only).
Akinturk et al., (2009) A clinical comparison of topical piroxicam and EMLA cream for pain relief and inflammation in laser hair removal. Lasers Med Sci. 24(4):535-538.
Alañón et al., (2014) Comparison between topical anaesthesia with cocaine versus lidocaine plus adrenaline for outpatient laser dacryocystorhinostomy. Arch Soc Esp Oftalmol. 89(2):53-57.

(56) References Cited

OTHER PUBLICATIONS

Allegrini et al., (2009) Efficacy and safety of piroxicam patch versus piroxicam cream in patients with lumbar osteoarthritis. A randomized, placebo-controlled study. Arzneimittelforschung. 59(8):403-409.
Alsarra, (2008) Evaluation of proniosomes as an alternative strategy to optimize piroxicam transdermal delivery. J Microencapsul. 26(3):272-278.
Altman et al., (2009) Topical therapy for osteoarthritis: clinical and pharmacologic perspectives. Postgrad Met 121(2):139-147. (Abstract Only).
Ambade et al., (2008) Formulation and evaluation of flurbiprofen microemulsion. Curr Drug Deliv. 5(1):32-41.
Ambler et al., (2005) the effect of topical non-steroidal anti-inflammatory cream on the incidence and severity of cutaneous burns following external DC cardioversion. Resuscitation. 65(2):173-178.
Arapoglou et al., (2011) Analgesic efficacy of an ibuprofen-releasing foam dressing compared with local best practice for painful exuding wounds. J Wound Care. 20(7):319-320, 322-325.
Argoff, (2004) Topical treatments for pain. Curr Pain Headache Rep. 8(4):261-267 (Abstract Only).
Arnau et al., (2013) Lidocaine-prilocaine (EMLA®) ) cream as analgesia in hysteroscopy practice: a prospective, randomized, non-blinded, controlled study. Acta Obstet Gynecol Scand. 92(8):978-981.
Ashfield, (2005) The use of topical opioids to relieve pressure ulcer pain. Nurs Stand. 19(45):90-92. (Abstract Only).
Assouline et al., (1998) A prospective randomized trial of topical soluble 0.1% indomethacin versus 0.1% diclofenac versus placebo for the control of pain following excimer laser photorefractive keratectomy. Ophthalmic Surg Lasers. 29 (5):365-374.
Attia et al., (2004) Transbuccal permeation, anti-inflammatory activity and clinical efficacy of piroxicam formulated in different gels. Int J Pharm. 276(1-2):11-28.
Audeval-Gerard et al., (2000) Pharmacokinetics of ketoprofen in rabbit after a single topical application. Eur J Drug Metab Pharmacokinet. 25(3-4):227-230. (Abstract Only).
Azevedo et al., (2000) Transdermal ketamine as an adjuvant for postoperative analgesia after abdominal gynecological surgery using lidocaine epidural blockade. Anesth Analg. 91(6):1479-1482.
B&B Compounding Pharmacy, (2010) Pain Management Compounding. Available at http://www.bbpharmacy.com/paincompounding.html. (5 pages).
Badalá et al., (2004) Effect of topical 0.1% indomethacin solution versus 0.1% fluorometholon acetate on ocular surface and pain control following laser subepithelial keratomileusis (LASEK). Cornea. 23(6):550-553.
Baixauli et al., (1990) Percutaneous treatment of acute soft tissue lesions with naproxen gel and ketoprofen gel. J Int Med Res. 18(5):372-378. (Abstract Only).
Barthel et al., (2009) Randomized controlled trial of diclofenac sodium gel in knee osteoarthritis. Semin Arthritis Rheum. 39(3):203-212.
Barton et al., (2011) A double-blind, placebo-controlled trial of a topical treatment for chemotherapy-induced peripheral neuropathy: NCCTG trial N06CA. Support Care Cancer. 19(6):833-841.
Bernstein et al., (1981) Inhibition of histamine-induced pruritus by topical tricyclic antidepressanants. J Am Acad Dermatol. 5(5):582-585.
Bhaskar et al., (2009) Lipid nanoparticles for transdermal delivery of flurbiprofen: formulation, in vitro, ex vivo and in vivo studies. Lipids Health Dis. 8:6.
Boardman et al., (2008) Topical gabapentin in the treatment of localized and generalized vulvodynia.Obstet Gynecol. 112(3):579-585.
Bourolias et al., (2010) Lidocaine spray vs tetracaine solution for transnasal fiber-optic laryngoscopy. Am J Otolaryngol. 31(2):114-116.
Campbell et al., (1994) Evaluation of topical ibuprofen cream in the treatment of acute ankle sprains. J Acid Emerg Med. 11(3):178-182.
Campione et al., (2010) Topical treatment of actinic keratoses with piroxicam 1% gel: a preliminary open-label study utilizing a new clinical score. Am J Clin Dermatol. 11(1):45-50.
Canbay et al., (2008) Topical ketamine and morphine for post-tonsillectomy pain. Eur J Anaesthesial. 25(4):287-292. (Abstract Only).
Christensen et al., (2013) Lidocaine analgesia for removal of wound vacuum-assisted closure dressings: a randomized double-blinded placebo-controlled trial. J Orthop Trauma. 27(2):107-112.
Cigna et al., (2009) Evaluation of polyurethane dressing with ibuprofen in the management of split-thickness skin gragraft donor sites. In Vivo. 23(6):983-936.
Conaghan et al., (2013) A multicentre, randomized, placebo- and active-controlled trial comparing the efficacy and safety of topical ketoprofen in Transfersome gel (IDEA-033) with ketoprofen-free vehicle (TDT 064) and oral celecoxib for knee pain associated with osteoarthritis. Rheumatology (Oxford). 52(7):1303-1312.
Cordero et al., (2001) In vitro based index of topical anti-inflammatory activity to compare a series of NSAIDs. Eur J Pharm Biopharm. 51(2):135-42. (Abstract Only).
Coudert et al., (2014) Phase III, randomized, double-blind, placebo-controlled trial of topical 2 % lidocaine for the prevention and treatment of oral mucosal pain in children. Clin Oral Investig. 18(4):1189-1194.
Crowley et al., (1998) Clinical application of ketamine ointment in the treatment of sympathetically maintained pain. Int J Pharm Compd. 2(2):122-127.
Dinsmore et al., (2007) Topical eutectic mixture for premature ejaculation (TEMPE): a novel aerosol-delivery form of idocaine-prilocaine for treating premature ejaculation. BJU Int. 99(2):369-375.
Dissanayake et al., (1997) Spermine modulation of specific [3H]-gabapentin binding to the detergent-solubilized porcine cerebral cortex alpha 2 delta calcium channel subunit. Br J Pharmacol. 120(5):833-840.
Dreiser et al., (1994) Flurbiprofen local action transcutaneous (LAT): clinical evaluation in the treatment of acute ankle sprains. Eur J Rheumatol Inflamm. 14(4):9-13.
Dutta et al., (2003) Piroxicam gel, compared to EMLA cream is associated with less pain after venous cannulation in volunteers. Can J Anaesth. 50(8):775-778.
EL Gendy et al., (2002) In vitro release studies of flurbiprofen from different topical formulations. Drug Dev Ind Pharm. 28(7):823-831.
Erickson, (2005) Can you provide a formulation for compounding meloxicam oral suspension? Pharmacy Times—Compoundingh-Hotline. Available at http://www.pharmacytimes.com/publications/issue/2005/2005-01/2005-01-9197.
Esparza et al., (2006) Topical ketoprofen TDS patch versus diclofenac gel: efficacy and tolerability in benign sport related soft-tissue injuries. Br J Sports Met 41(3):134-139.
Federal Drug Agency, (1996) TOPAMAX—Highlights of Prescribing Information. (27 pages).
Federal Drug Agency, (2010) MOBIC—Highlights of Prescribing Information. (15 pages).
Fibromyalgia General Discussion—"So Many Questions—Please Read and Advise" (Jan. 15, 2011), available at http://www.fibromyalgia-symptoms.org/forums/fibromyalgia_general_discussion/so_many_questions_please_read_and_advise/.
Fraczek et al., (2012) Assessment of the efficacy of topical anesthetics using the tactile spatial resolution method. Acta Dermatovenerol Croat. 20(1):7-13.
Franchi et al., (2009) Comparison between lidocaine-prilocaine cream (EMLA) and mepivacaine infiltration for pain relief during perineal repair after childbirth: a randomized trial. Am J Obstet Gynecol. 201(2)186.e1-5.
Franz et al., (1990) The use of water permeability as a means of validation for skin integrity in in vitro percutaneous-absorption studies. J Invest Dermatol. 94(4):525. (Abstract Only).
Franz et al., (2008) The cadaver skin absorption mode and the drug development process. Pharmacopeial Forum. 34 (5).

(56) References Cited

OTHER PUBLICATIONS

Franz et al., (2009) Use of excised human skin to assess the bioequivalence of topical products. Skin Pharmacol Physiol. 22(5):276-286.
Franz, (1975) Percutaneous absorption on the relevance of in vitro data. J Invest Dermatol. 64(3):190-195.
Funosas et al., (2009) The use of topical subgingival gels of non-steroidal anti-inflammatory drugs (NSAIDs) as an adjunct to non-surgical management of chronic periodontitis. Acta Odontol Latinoam. 22(3):215-219.
Gammaitoni et al., (2007) Topical ketamine gel: possible role in treating neuropathic pain. Pain Med. 1(1):97-100.
Gaviola et al., (2013) A prospective, randomized, double-blind study comparing the efficacy of topical anesthetics in nasal endoscopy. Laryngoscope. 123(4):852-858.
Gencer et al., (2013) Comparison of ropivacaine, bupivacaine, prilocaine, and lidocaine in the management of pain and hemorrhage during nasal pack removal. Am J Rhinol Allergy. 27(5):423-425.
Gennaro, (Editor) (1995) Remington: Practice of The Science and Pharmacy (19th Edition) (Philadelphia, PA Lippincott Williams & Wilkins)—Chapter 66 (pp. 1516-1517).
Gerbino, (1995) Remington: Practice of the Science and Pharmacy (21st Edition) (Philadelphia, PA: Lippincott Williams & Wilkins)—Chapter 39 (pp. 745-747, 759-760, 768-770), Chapter 44 (871-877).
Gerner et al., (2003) Topical amitriptyline in healthy volunteers. Reg Anesth Pain Med. 28(4)289-293.
Ginsberg et al., (1991) Double-blind, randomized crossover study of the percutaneous efficacy and tolerability of a topical indomethacin spray versus placebo in the treatment of tendinitis. J Int Med Res. 19(2):131-136.
Guindon et al., (2007) Recent advances in the pharmacological management of pain. Drugs. 67(15):2121-2133. (Abstract Only).
Gupta et al., (2013) Randomized controlled trial of topical EMLA and breastfeeding for reducing pain during wDPT vaccination. Eur J Pediatr. 172(11):1527-1533.
Gursoy et al., (2007) The analgesic efficacy of lidocaine/prilocaine (EMLA) cream during fine-needle aspiration biopsy of thyroid nodules. Clin Endocrinol (Oxf). 66(5):691-694.
Heir et al., (2008) Use of topical medication in orofacial neuropathic pain: a retrospective study. Oral Surg Oral Med Oral Pathol Oral Radiol Endod. 105(4):466-469. (Abstract Only).
Hirsh et al., (2007) Tramadol improves patients tolerance of transrectal ultrasound-guided prostate biopsy. Urology. 69(3):491-494.
Hong et al., (2014) Comparison of analgesic effect of preoperative topical diclofenac and ketorolac on postoperative pain after photorefractive keratectomy. J Cataract Refract Surg. 40(10):1689-1696.
Hong et al., (2003) Suprascapular nerve block or a piroxicam patch for shoulder tip pain after day case laparoscopic surgery. Eur J Anaesthesiol. 20(3):234-8. Erratum in: Eur J Anaesthesiol. (2003) 20(5):426. (Abstract Only).
Hopp et al., (2012) Clinical efficacy of tetracaine anesthetic paste. Gen Dent. 60(2):e69-73. (Abstract Only).
Hui-Chen et al., (2013) The effect of EMLA cream on minimizing pain during venipuncture in premature infants. J Trop Pediatr. 59(1):72-73.
Keppel Hesselink et al., (2013) Treatment of chronic regional pain syndrome type 1 with palmitoylethanolamide and topical ketamine cream: modulation of nonneuronal cells. J Pain Res. 6:239-245.
Kneer et al., (2009) A multiple-dose, open-label, safety, compliance, and usage evaluation study of epicutaneously applied Diractin (ketoprofen in Transfersome) in joint/musculoskeletal pain or soft tissue inflammation. Curr Drug Saf. 4 (1):5-10.
Kolesnikov et al., (2008) Analgesic synergy between topical opioids and topical non-steroidal anti-inflammatory drugs in the mouse model of thermal pain. Eur J Pharmacol. 579(1-3):126-133. (Abstract Only).
Kronenberg, (2002) Ketamine as an analgesic: parenteral, oral, rectal, subcutaneous, transdermal and intranasal administration. J Pain Palliat Care Pharmacother. 16(3):27-35. (Abstract Only).
Kwon et al., (2012) Treatment for postoperative wound pain in gynecologic laparoscopic surgery: topical lidocaine patches. J Laparoendosc Adv Surg Tech A. 22(7):668-673.
Lee et al., (2013) The effect of buffered lidocaine in local anesthesia: a prospective, randomized, double-blind study. J Hand Surg Am. 38(5):971-975.
Lehman et al., (2008) Effective use of topical amitriptyline hydrochloride 2.5% and ketamine hydrochloride 0.5% for analgesia in refractory proctodynia. J Drugs Dermatol. 7(9):887-889. (Abstract Only).
Lehmann et al., (1996) Meloxicam: A toxicology overview. InflammoPharmacology. 4(2):105-123. (Abstract Only).
Liang et al., (2011) Topical anesthetic EMLA for postoperative wound pain in stereotactic gamma knife radiosurgery: a perspective, randomized, placebo-controlled study. Minim Invasive Neurosurg. 54(2):75-78.
Liberty et al., (2007) Lidocaine-prilocaine (EMLA) cream as analgesia for hysterosalpingography: a prospective, randomized, controlled, double blinded study. Hum Reprod. 22(5):1335-1339.
Lynch et al., (2003) A pilot study examining topical amitriptyline, ketamine, and a combination of both in the treatment of neuropathic pain. Clin J Pain. 19(5):323-328.
Lynch et al., (2005) Topical 2% amitriptyline and 1% ketamine in neuropathic pain syndromes: a randomized, double-blind, placebo-controlled trial. Anesthesiology. 103(1):140-146.
Lynch et al., (2005) Topical amitriptyline and ketamine in neuropathic pain syndromes: an open-label study. J Pain. 6(10):644-649.
Machen et al., (2002) Efficacy of a proprietary ibuprofen gel in soft tissue injuries: a randomised, double-blind, placebo-controlled study. Int J Clin Pract. 56(2):102-106.
Mansell-Gregory et al., (1998) Randomised double blind trial of EMLA for the control of pain related to cryotherapy in the treatment of genital HPV lesions. Sex Transm Infect. 74(4):274-275.
Marks et al., (1994) Plasma and cutaneous drug levels after topical application of piroxicam gel: a study in healthy volunteers. Skin Pharmacol. 7(6):340-344. (Abstract Only).
Martens, (1997) Efficacy and tolerability of a topical NSAID patch (local action transcutaneous flurbiprofen) and oral diclofenac in the treatment of soft-tissue rheumatism. Clin Rheumatol. 16(1):25-31.
Matucci-Cerinic et al., (1988) Ketoprofen vs etofenamate in a controlled double-blind study: evidence of topical effectiveness in soft tissue rheumatic pain. Int J Clin Pharmacol Res. 8(3):157-160. (Abstract Only).
Mazières et al., (2005) Topical ketoprofen patch (100 mg) for the treatment of ankle sprain: a randomized, double-blind, placebo-controlled study. Am J Sports Med. 33(4):515-523.
Mazières et al., (2005) Topical ketoprofen patch in the treatment of tendinitis: a randomized, double blind, placebo controlled study. J Rheumatol. 32(8):1563-1570.
Mazières, (2005) Topical ketoprofen patch. Drugs R D. 6(6):337-344. (Abstract Only).
Merskey, (1997) Pharmacological approaches other than opioids in chronic non-cancer pain management. Acta Anaesthesiol Scand. 41(1 Pt 2):187-190. (Abstract Only).
Missotten, et al., (2001) Topical 0.1% indomethacin solution versus topical 0.1% dexamethasone solution in the prevention of inflammation after cataract surgery. The Study Group. Ophthalmologica. 215(1):43-50.
Moen, (2009) Topical diclofenac solution. Drugs. 69(18):2621-2632.
Moghadamnia et al., (2009) Evaluation of the effect of locally administered amitriptyline gel as adjunct to local anesthetics in irreversible pulpitis pain. Indian J Dent Res. 20(1):3-6. (Abstract Only).
Momo et al., (2005) Preparation and clinical application of indomethacin gel for medical treatment of stomatitis. Yakugaku Zasshi. 125(5):433-440.

(56) References Cited

OTHER PUBLICATIONS

Moretti et al., (2000) In vitro release and antiinflammatory activity of topical formulations of ketoprofen. Boll Chim Farm. 139(2):67-72. (Abstract Only).

Nahata et al., (1999) Stability of lamotrigine in two extemporaneously prepared oral suspensions at 4 and 25 degrees C. Am J Health Syst Pharm. 56(3):240-242. (Abstract Only).

* cited by examiner

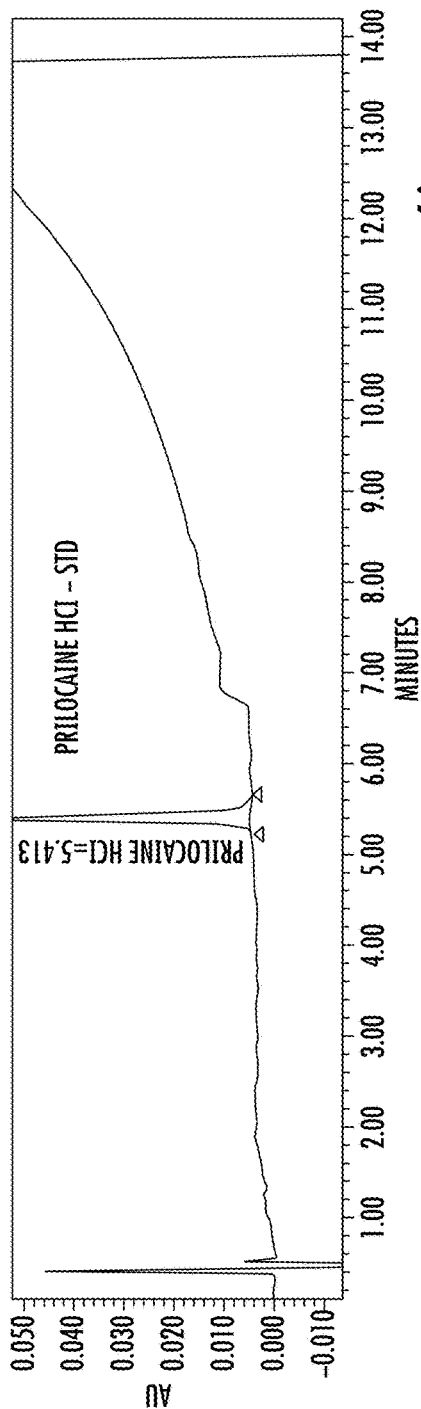
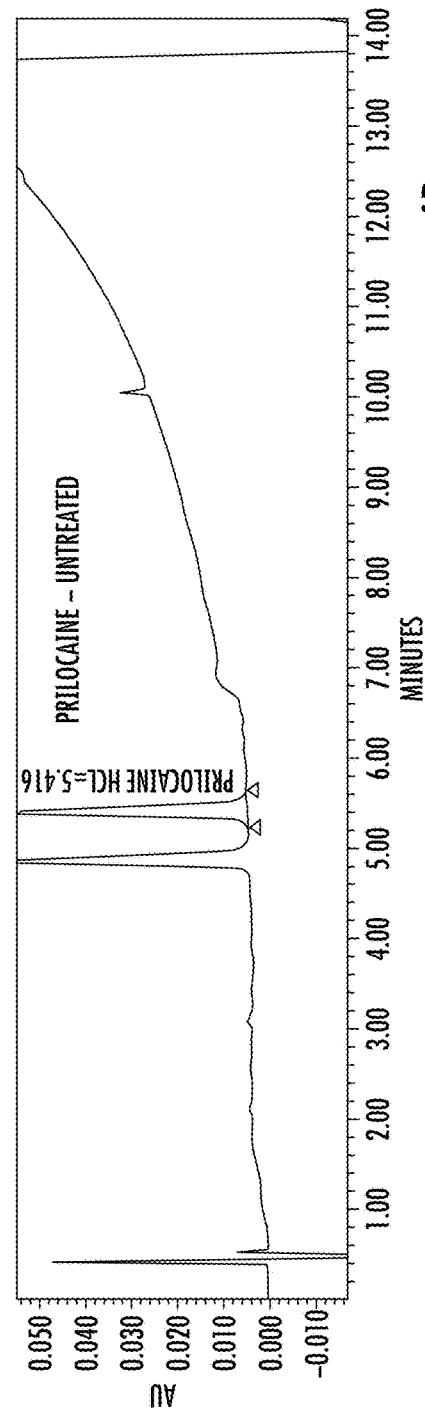
FIG. 4A
FIG. 4B

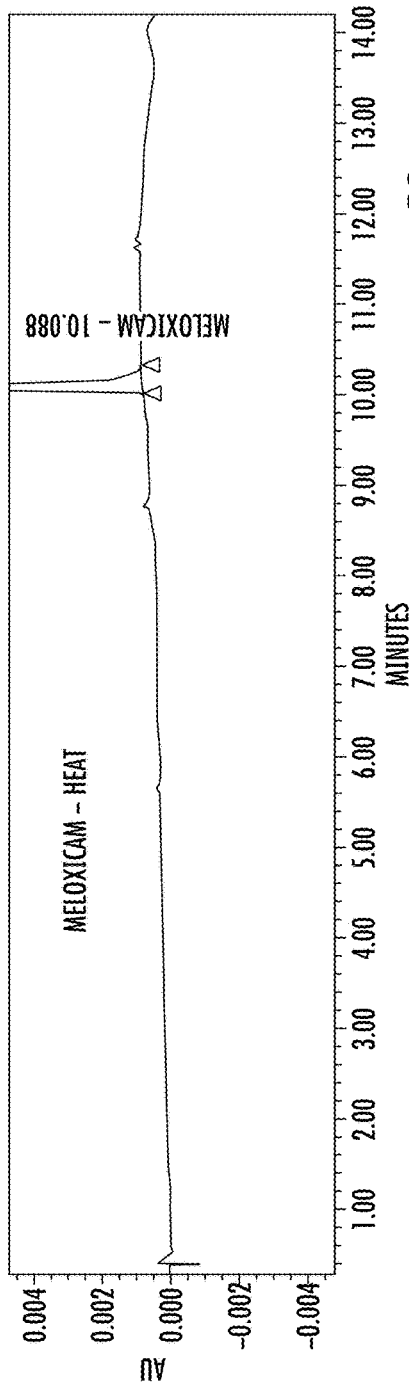
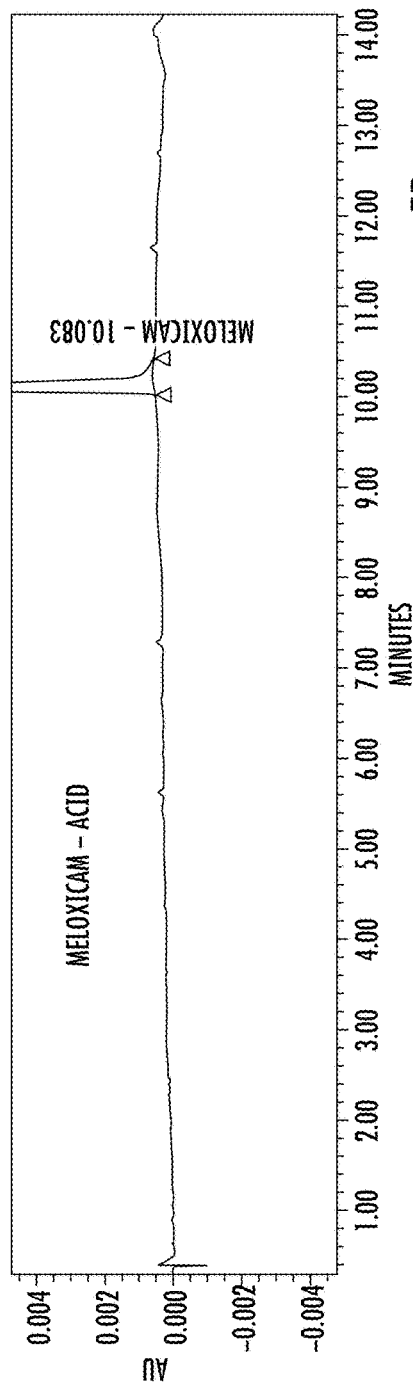

COMPOSITION AND METHOD FOR COMPOUNDED THERAPY

CROSS-REFERENCE TO RELATED APPLICATIONS

This patent application is a continuation in-part of co-pending U.S. patent application Ser. No. 14/996,560, entitled Composition and Method for Compounded Therapy, filed Jan. 15, 2016, which is a continuation-in-part of U.S. patent application Ser. No. 13/448,088 (now U.S. Pat. No. 9,468,599), entitled Composition and Method for Compounded Therapy, filed Apr. 16, 2012, which is a continuation of U.S. patent application Ser. No. 13/409,738, entitled Composition and Method for Compounded Therapy, filed Mar. 1, 2012, now abandoned, which is a continuation-in-part of U.S. patent application Ser. No. 13/337,598, entitled Composition and Method for Compounded Therapy, filed Dec. 27, 2011, now abandoned.

FIELD OF THE INVENTION

The present application relates to compounded therapies. In particular, the present application relates to compositions for compounded therapy and methods of compounding medications.

BACKGROUND

Transdermal creams are employed to deliver medication to the skin of a patient. Conventional compositions intended for topical administration include EMLA cream, a eutectic mixture of lidocaine and prilocaine in an emulsified topical cream, such as disclosed by U.S. Pat. Nos. 6,299,902 and 4,562,060, which are incorporated herein by reference in their entireties. However, conventional transdermal creams may include various drawbacks, such as addressing limited medical conditions, creating adverse side effects, and/or having limited shelf lives. Additionally, conventional methods of manufacturing transdermal creams may be inefficient and/or lack precision with the amount of active ingredients, or have other drawbacks.

SUMMARY

In one aspect, a method of making a compounded transdermal cream includes grinding up one or more tablets of a Non-Steroidal Anti-Inflammatory Drug (NSAID) to produce a fine powder, wherein the NSAID comprises meloxicam. The method also includes grinding up one or more tablets of one or more nerve depressants, anticonvulsants, or combinations thereof to produce a fine powder, wherein the one or more nerve depressants anticonvulsants, or combinations thereof comprises gabapentin. The method may also include wetting the ground fine powders with a wetting agent and adding the wetted ground fine powders to a eutectic mixture of lidocaine and prilocaine in an emulsified topical cream in the form of a lidocaine 2.5%-prilocaine 2.5% cream to form a compounded transdermal cream. The compounded transdermal comprises between 0.05% and 0.15% by weight meloxicam, between 1.0% and 5.0% by weight gabapentin, and 80% or more by weight of the eutectic mixture comprising lidocaine and prilocaine in an emulsified topical cream in the form of a lidocaine 2.5%-prilocaine 2.5% cream.

In one example, the compounded transdermal cream comprises 0.09% by weight meloxicam. The compounded transdermal cream may further include 2.15% by weight of each of lidocaine and prilocaine. In one example, the compounded transdermal cream includes approximately 2.5% by weight gabapentin. The compounded transdermal cream may further include 2.15% by weight of each of lidocaine and prilocaine. In one example, the compounded transdermal cream includes 0.09% by weight meloxicam and 2.5% by weight gabapentin. The compounded transdermal cream may include 2.15% by weight of each of lidocaine and prilocaine. The wetting agent may be purified water.

A milled mixture may comprise a compounded transdermal cream. The milled mixture may include one or more Non-Steroidal Anti-Inflammatory Drug (NSAID) tablets or portion thereof. The one or more NSAID tablets or portion thereof may include meloxicam tablets or portion thereof in an amount sufficient to obtain between 0.05% and 0.15% by weight meloxicam in the milled mixture. The milled mixture may further include one or more nerve depressant tablets or portion thereof. The one or more nerve depressant tablets or portion thereof may include gabapentin tablets or portion thereof in an amount sufficient to obtain between 1.0% and 5.0% by weight gabapentin. The milled mixture may further include an eutectic mixture of lidocaine and prilocaine in an emulsified topical cream in the form of a lidocaine 2.5%-prilocaine 2.5% cream. The milled mixture may include 80% or more by weight lidocaine 2.5%-prilocaine 2.5% cream.

In one example, the milled mixture includes 0.09% by weight meloxicam. The milled mixture may further include 2.15% by weight of each of lidocaine and prilocaine. In one example, the milled mixture may include approximately 2.5% by weight gabapentin. The milled mixture may further include 2.15% by weight of each of lidocaine and prilocaine. In one example, the milled mixture includes 0.09% by weight meloxicam and 2.5% by weight gabapentin. The milled mixture may further include 2.15% by weight of each of lidocaine and prilocaine.

The above-described and other features and advantages of the present disclosure will be appreciated and understood by those skilled in the art from the following detailed description, drawings, and appended claims.

BRIEF DESCRIPTION OF THE DRAWINGS

There is shown in the drawings embodiments which are presently preferred, it being understood, however, that the invention can be embodied in other forms without departing from the spirit or essential attributes thereof.

FIGS. 4A-4D present exemplary chromatograms of standard, untreated, heat treated, and acid treated Prilocaine samples, respectively, generated in a degradation study according to various embodiments described herein;

FIGS. 5A-5D present exemplary chromatograms of standard, untreated, heat treated, and acid treated Meloxicam samples, respectively, generated in a degradation study according to various embodiments described herein;

DETAILED DESCRIPTION OF THE INVENTION

Figure 1:
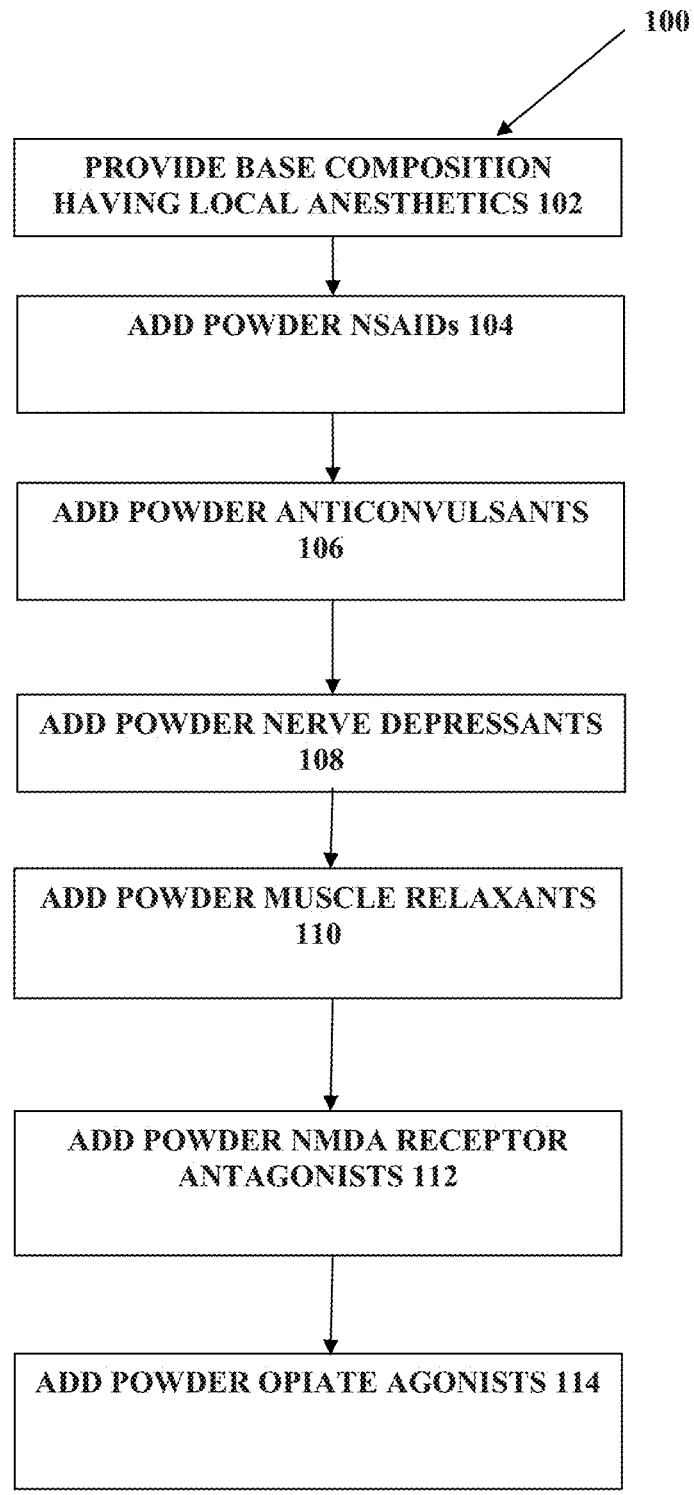
FIG. 1 depicts an exemplary method of compounding according to various embodiments described herein.

The present embodiments may relate to topically delivered compounded medications for treatment of various ailments, such as pain, osteoarthritis, epilepsy, inflammation, muscle fatigue, spasms, and/or other ailments. In one aspect, a transdermal cream for the effective administration of multiple medications simultaneously for one or more ailments may be provided. The transdermal cream may include low concentrations of lidocaine, prilocaine, meloxicam, lamotrigine and/or topiramate, and other active ingredients.

Alternatively, the transdermal cream may include a base having both lidocaine and prilocaine, and to which is added a fine powder of one or more medications. The medication in fine powder form may be generated from grinding up tablets of NSAIDs (Non-Steroidal Anti-Inflammatory Drugs), anticonvulsants, nerve depressants, muscle relaxants, NMDA (N-Methyl-D-aspartate) receptor antagonists, opiate or opioid agonists, antidepressants, and/or other active agents. The fine powder may allow for precise amounts of the active ingredients to be added to the base. The transdermal cream may exhibit excellent storage characteristics, and avoid separation and/or degradation of the active ingredients from the base for substantial lengths of time.

In one aspect, a transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and lamotrigine and/or topiramate in an amount between approximately 0.5% and approximately 5.0% by weight of the transdermal cream. As a result, the transdermal cream may allow for the topical administration of lidocaine, prilocaine, meloxicam, and lamotrigine and/or topiramate simultaneously during use. In one embodiment, the transdermal cream may comprise approximately 2.0% by weight lidocaine and prilocaine, respectively; approximately 0.09% by weight meloxicam; and approximately 2.5% by weight either lamotrigine or topiramate.

In another aspect, a method of compounding one or more medications with a transdermal cream for the topical administration of a compounded therapy may be provided. The method may include grinding up one or more tablets of a NSAID, an anticonvulsant, a nerve depressant, a muscle relaxant, a NMDA receptor antagonist, antidepressant, and/or an opiate or opioid agonist into a fine powder of medication. The method may also include adding the fine powder of medication to a transdermal cream containing both lidocaine and prilocaine, the transdermal cream including both lidocaine and prilocaine in an amount of between approximately 0.5% and approximately 7.0% by weight of the transdermal cream. The method may include adding the fine powder of medication to the transdermal cream in a sufficient amount such that the transdermal cream includes the medication that is ground up in an amount of between approximately 0.01% and approximately 5.0% by final weight of the transdermal cream.

The fine powder may be a fine powder of compounded medication that includes two or more active ingredients. For example, the active ingredients may comprise a NSAID, such as meloxicam, and a nerve depressant or an anticonvulsant, such as lamotrigine and/or topiramate. In one embodiment, an amount of ground up compounded medication is added to the base such that the final composition of the transdermal cream after the fine powder of compounded medication is added is approximately 2.0% by weight lidocaine, approximately 2.0% by weight prilocaine, approximately 0.09% by weight meloxicam, and approximately 2.5% by weight either lamotrigine or topiramate.

I. Compositions for Compounded Therapy

The present embodiments may relate to a compounded medication program. The compounded medication program may address several ailments simultaneously. In one aspect, the present embodiments may be intended to minimize skin damage or irritation caused by the topical administration of various medications. Administering low doses or applying transdermal creams or gels with low concentrations of one or more active ingredients may minimize adverse side effects, such as side effects that develop with prolonged usage.

For instance, Stevens-Johnson Syndrome (SJS) and toxic epidermal necrolysis (TEN) are two forms of life-threatening skin conditions. SJS is a potentially deadly skin disease that usually results from a drug reaction. Drugs that have been linked to SJS include, but are not limited to: NSAIDs, allopurinol, phenytoin, carbamazepine, barbiturates, anticonvulsants, and sulfa antibiotics. However, almost any drug (prescription or over-the-counter) could potentially cause SJS if a severe enough allergy is present.

The onset of severe symptoms in drug related SJS may not appear for 1-2 weeks after first taking the drug causing the allergic reaction. Initial non-specific symptoms such as coughing, aching, headaches, fevers, vomiting, and diarrhea are commonly seen. These symptoms are usually followed by a red rash across the face and trunk of the body, later followed by blisters, and in some situations the nails and hair begin to fall out.

SJS is a very serious and potentially deadly condition and should be treated accordingly. Discontinuation of the medication and treatment of the "new infection" with a suitable antibiotic is the first step. In some situations, a patient is treated in a burn unit if necessary. However, compounded therapies may administer lower doses of active agents topically, and thus the effect of any adverse skin reaction may be lowered due to the lower doses of agent that the patient is allergic to.

In view of the foregoing, the present embodiments may include providing, within a base composition, several medications that address different ailments. The medications may be mixed in low concentrations to minimize any adverse reaction to the topical cream or gel containing the several medications.

The medications may be mixed with the base composition for topical administration to a patient. The medications may include one or more local anesthetics, such as lidocaine, prilocaine, or benzocaine; one or more NSAIDs, such as meloxicam; and one or more nerve depressants and/or anticonvulsants, such as gabapentin, topiramate, or lamotrigine. The medications may also include one or more muscle relaxants, such as baclofen or cyclobenzaprine; one or more NMDA receptor antagonists, such as ketamine; and/or one or opiate or opioid agonists, such as C2 or C3 opiate agonists, or tramadol.

II. Meloxicam/Lamotrigine/Lidocaine/Prilocaine Compounded Medication

In one aspect, a transdermal cream or gel may include lidocaine, prilocaine, meloxicam, and lamotrigine. Lidocaine and prilocaine are amide-type local anesthetic agents. They may come in commercially available creams.

The amount of lidocaine and prilocaine in the transdermal cream may be approximately the same. The amount of lidocaine and prilocaine may each be between approximately 0.5% and approximately 5.0% of the total weight of the transdermal cream. Alternatively, the amount of lidocaine and prilocaine may each be between approximately 1.0% and approximately 4.0% of the total weight of the transdermal cream, or between approximately 1.5% and approximately 3.0% of the total weight of the transdermal cream. In one preferred embodiment, the amount of lidocaine and prilocaine may each be approximately 2.0% of the total weight of the final transdermal cream or gel.

Meloxicam is a NSAID that may provide pain relief, such as pain relief for osteoarthritis or rheumatoid arthritis. In one aspect, the amount of meloxicam in the transdermal cream or gel may be less than that of the other active ingredients.

The amount of meloxicam in the transdermal cream may be between approximately 0.01% and approximately 5.0% of the total weight of the transdermal cream, or between approximately 0.03% and approximately 3.0% of the total weight of the transdermal cream. Preferably, the amount of meloxicam may be between approximately 0.05% and approximately 0.15% of the total weight of the transdermal cream. In one preferred embodiment, the amount of meloxicam may be approximately 0.09% of the total weight of the transdermal cream or gel.

Lamotrigine may be characterized as an anticonvulsant. It may be used as an antiepileptic drug to treat epilepsy or bi-polar disorders. In one aspect, the amount of lamotrigine in the transdermal cream or gel may be more than the other active ingredients, such as lidocaine, prilocaine, meloxicam, and/or other active ingredients.

The amount of lamotrigine in the transdermal cream may be between approximately 0.5% and approximately 5.0% of the total weight of the transdermal cream, or between approximately 1.5% and approximately 3.5% of the total weight of the transdermal cream. Preferably, the amount of lamotrigine may be between approximately 2.0% and approximately 3.0% of the total weight of the transdermal cream. In one preferred embodiment, the amount of lamotrigine may be approximately 2.5% of the total weight of the transdermal cream or gel.

III. Meloxicam/Topiramate/Lidocaine/Prilocaine Compounded Medication

In one aspect, a transdermal cream or gel may include lidocaine, prilocaine, meloxicam, and topiramate. The amounts of lidocaine, prilocaine, and meloxicam may be as stated above. Alternatively, other amounts of lidocaine, prilocaine, and meloxicam may be used.

Topiramate may be characterized as an antiepileptic drug used to treat epilepsy or migraines. In one aspect, the amount of topiramate in the transdermal cream or gel may be more than the other active ingredients, such as lidocaine, prilocaine, meloxicam, and/or other active ingredients.

The amount of topiramate in the transdermal cream may be between approximately 0.5% and approximately 5.0% of the total weight of the transdermal cream, or between approximately 1.5% and approximately 3.5% of the total weight of the transdermal cream. Preferably, the amount of topiramate may be between approximately 2.0% and approximately 3.0% of the total weight of the transdermal cream. In one preferred embodiment, the amount of topiramate may be approximately 2.5% of the total weight of the transdermal cream or gel.

IV. Exemplary Method of Compounding

FIG. 1 depicts an exemplary method of compounding one or more medications with a transdermal cream or gel 100. The method 100 may include providing a base composition having one or more local anesthetics 102; and adding to the base a fine powder of medication comprising: one or more NSAIDs 104; one or more anticonvulsants 106; one or more or nerve depressants 108; one or more muscle relaxants 110; one or more NMDA receptor antagonists 112; and/or one or more opiate or opioid agonists 114. The transdermal cream or gel may include additional, fewer, or alternate steps and/or ingredients.

The method 100 may comprise providing a base composition 102. The base composition may comprise one or more local anesthetics 102. Primary examples of local anesthetics that the transdermal creams and base composition disclosed herein may employ include, but are not limited to, lidocaine, prilocaine, benzocaine, and/or tetracaine. The local anesthetics may comprise between approximately 0.1% and approximately 5.0% by weight of the transdermal cream. Other amounts may be used, including those discussed elsewhere herein. The base composition may include additional, fewer, or alternate ingredients.

Preferably, the base composition may include lidocaine and/or prilocaine. In one embodiment, the base composition may comprise an equal amount of lidocaine and prilocaine, such as between approximately 2.0% and approximately 3.0% by weight of the transdermal cream. Other amounts may be used, including those discussed elsewhere herein.

The method 100 may comprise adding to the base composition a fine powder of medication that includes one or more NSAIDs 104. NSAIDs may decrease inflammation, swelling, and pain. NSAIDs that may be added to the base composition may include: (1) oxicams—meloxicam and piroxicam; (2) salicylic acid derivatives—aspirin, diflunisal, salsalate, and trilisate; (3) propionic acids—flurbiprofen, ibuprofen, ketoprofen, naproxen, and oxaprozin; (4) acetic acids—diclofenac, etodolac, indomethacin, ketorolac, nabumetone, sulindac, and tolmetin; (5) fenamates—meclofenamate; and/or (6) COX-2 inhibitors—celecoxib, rofecoxib, and valdecoxib. Preferably, the final transdermal cream may comprise a low concentration of an oxicam, such as meloxicam or piroxicam, in a low amount between approximately 0.01% and 5.0% by weight of the final transdermal cream. In one embodiment, the final transdermal cream may include approximately 0.09% meloxicam by weight. Other amounts may be used, including those discussed elsewhere herein.

The method 100 may comprise adding to the base composition a fine powder of medication that includes one or more anticonvulsants 106. Anticonvulsants that may be added to the base composition may include lamotrigine and/or topiramate. The final transdermal cream may include an anticonvulsant in a low amount between approximately 0.1% and approximately 5.0% by weight of the final transdermal cream. Preferably, the final transdermal cream may comprise approximately 2.5% of either lamotrigine or topiramate by weight. Other amounts may be used, including those discussed elsewhere herein.

The method 100 may comprise adding to the base composition a fine powder of medication that includes one or more nerve depressants 108. Nerve depressants that may be added to the base composition may include gabapentin and/or others. The low amount of nerve depressant in the transdermal cream may be between approximately 0.1% and approximately 5.0% of the total weight of the transdermal cream. Other amounts may be used.

The method 100 may comprise adding to the base composition a fine powder of medication that includes one or more muscle relaxants 110. The active ingredients that may be added to the base compositions in form of fine powder may comprise baclofen, carisoprodol, chlorzoxazone, cyclobenzaprine, dantrolene, diazepam, metaxalone, methocarbamol, orphenadrine, quinine sulfate, tizanidine, and/or other muscle relaxants. The low amount of muscle relaxant in the transdermal cream may be between approximately 0.1% and approximately 5.0% of the total weight of the transdermal cream. Other amounts may be used.

The method 100 may comprise adding to the base composition a fine powder of medication that includes one or more NMDA receptor antagonists 112, such as ketamine. Ketamine may be useful because of its NMDA receptor activity (antagonism). The low amount of NMDA receptor antagonist in the transdermal cream may be between approximately 0.1% and approximately 5.0% of the total weight of the transdermal cream. Other amounts may be used.

The method 100 may comprise adding to the base composition a fine powder of medication that includes one or more opiate or opioid agonists 114. C2 opiate agonists may include oxycodone, morphine, methadone, hydromorphone, and fentanyl. C3 opiate agonists may include hydrocodone, codeine, propoxyphene, butalbital, and pentazocine. The active ingredients that may be added to the base composition in the form of fine powder may include the C2 and C3 opiate agonists named above and/or tramadol. The low amount of opiate or opioid agonist in the transdermal cream may be between approximately 0.1% and approximately 5.0% of the total weight of the transdermal cream. Other amounts may be used.

V. Another Exemplary Method of Compounding

A method of compounding medications with a base composition using a fine powder of medication is disclosed herein. In general, a base composition, such as a lidocaine/prilocaine cream, should be selected. The preparer, such as a pharmacist, should calculate the weight of powders needed. Then, the prepare should grind the medication, such as tablets containing the medication, into fine powder and weigh the ingredients. The preparer should triturate the powders together and wet with dimethyl sulfoxide (DMSO) or Sterile Water for Irrigation. The preparer should bring to total weight with the lidocaine/prilocaine cream and mix well. The mixture should be milled in an ointment mill as necessary to acquire the desired consistency. After which, the preparer should mix thoroughly and package appropriately.

Figure 2:
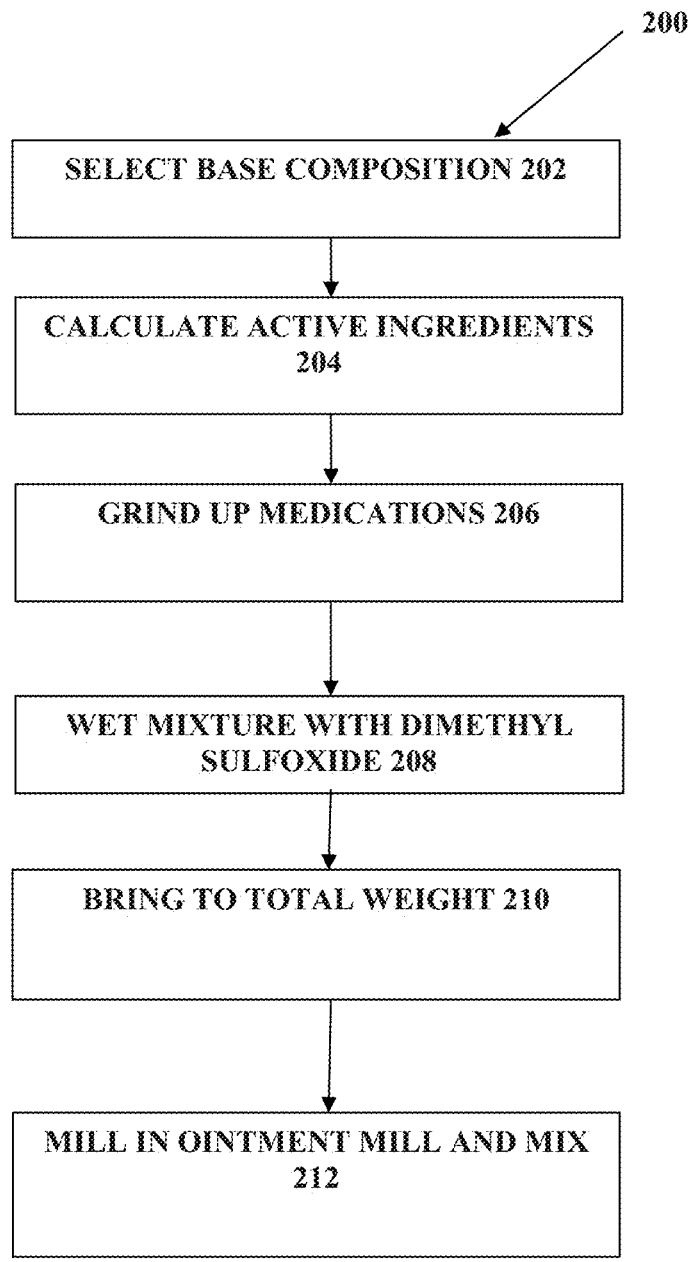
FIG. 2 depicts another exemplary method of compounding according to various embodiments described herein.
Figure 3A:
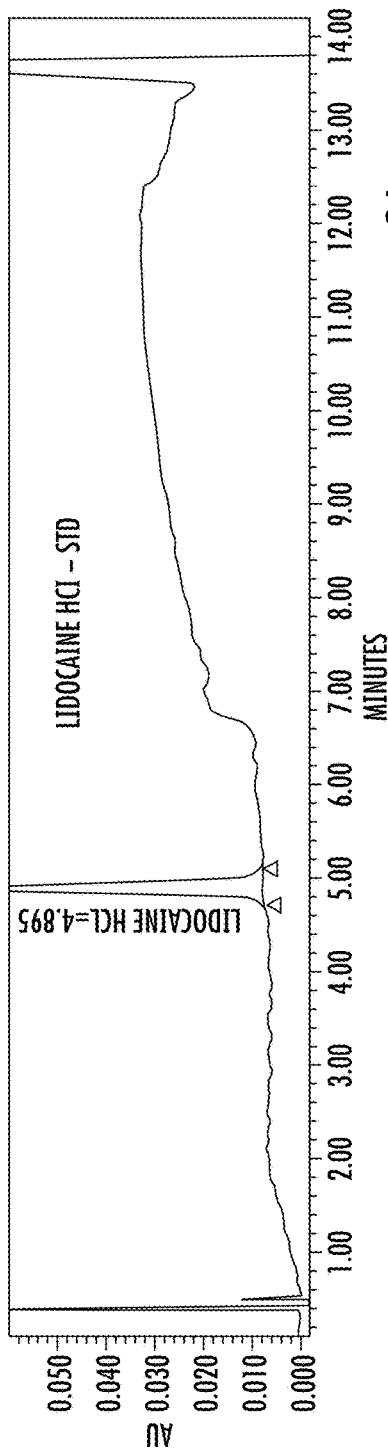
FIGS. 3A-3D present exemplary chromatograms of standard, untreated, heat treated, and acid treated Lidocaine samples, respectively, generated in a degradation study according to various embodiments described herein.
Figure 3B:
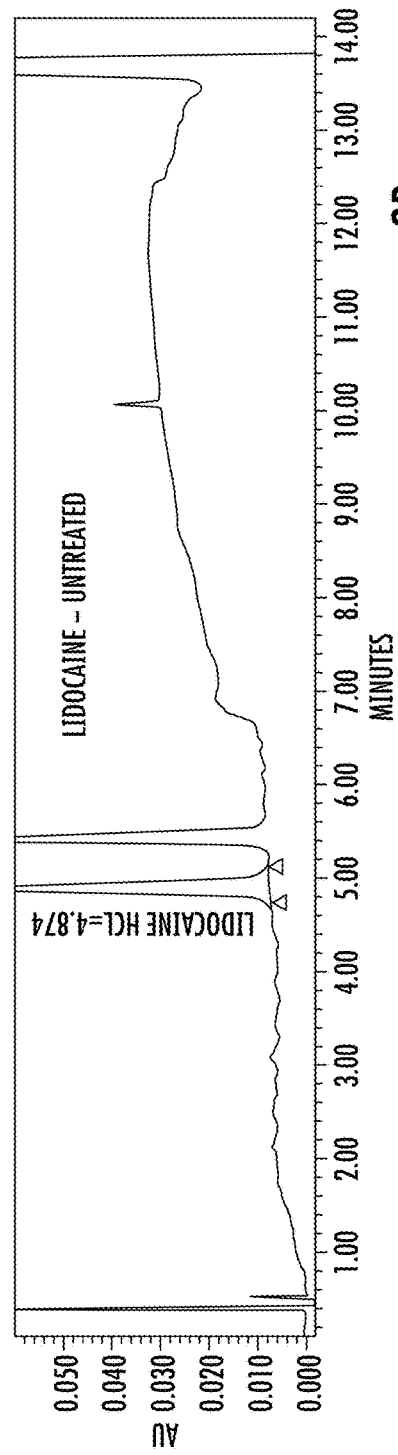
Figure 3C:
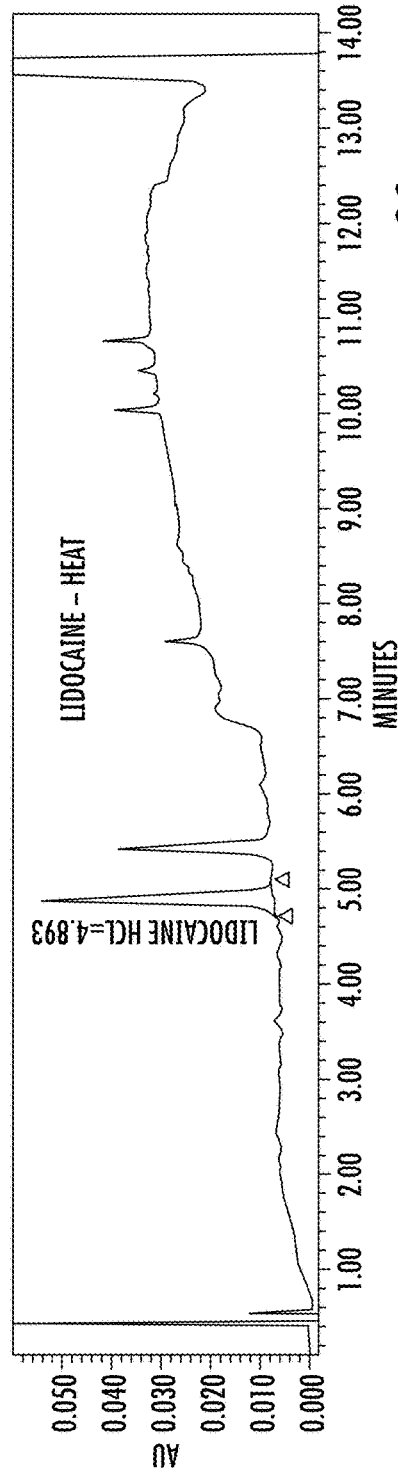
Figure 3D:
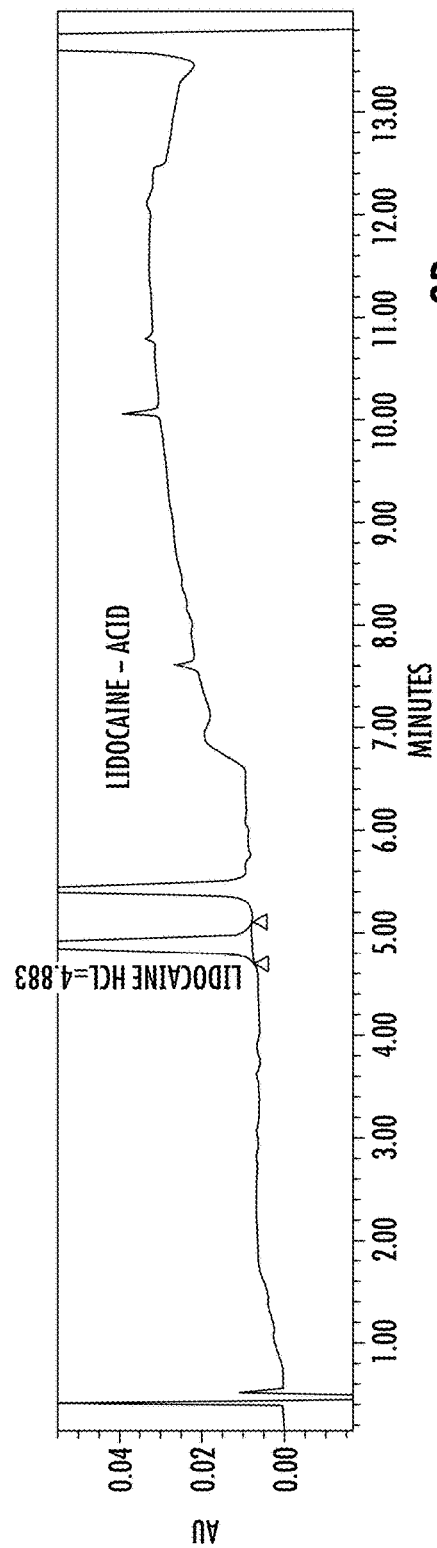
Figure 4C:
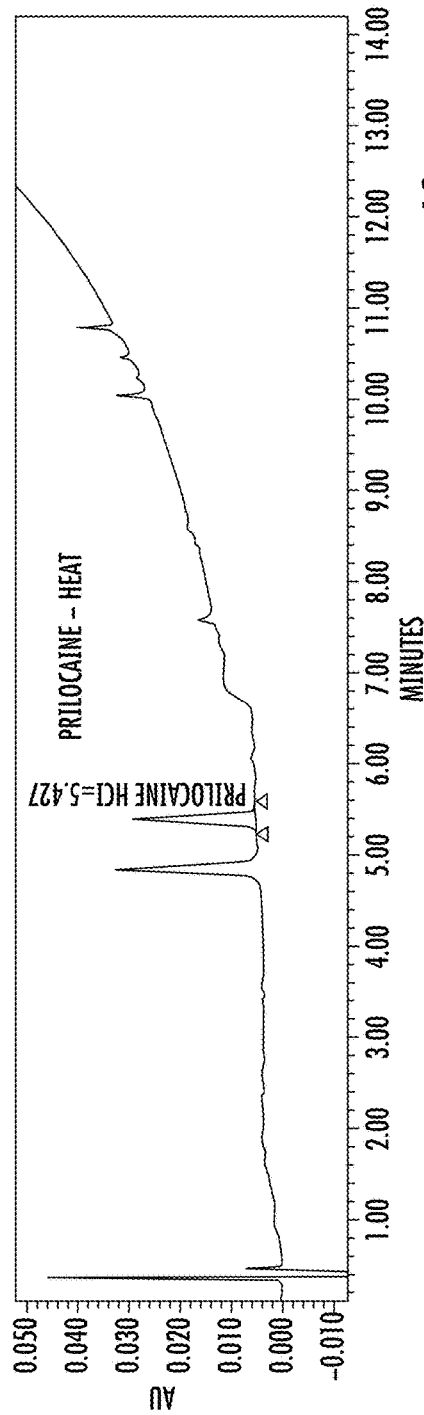
Figure 4D:
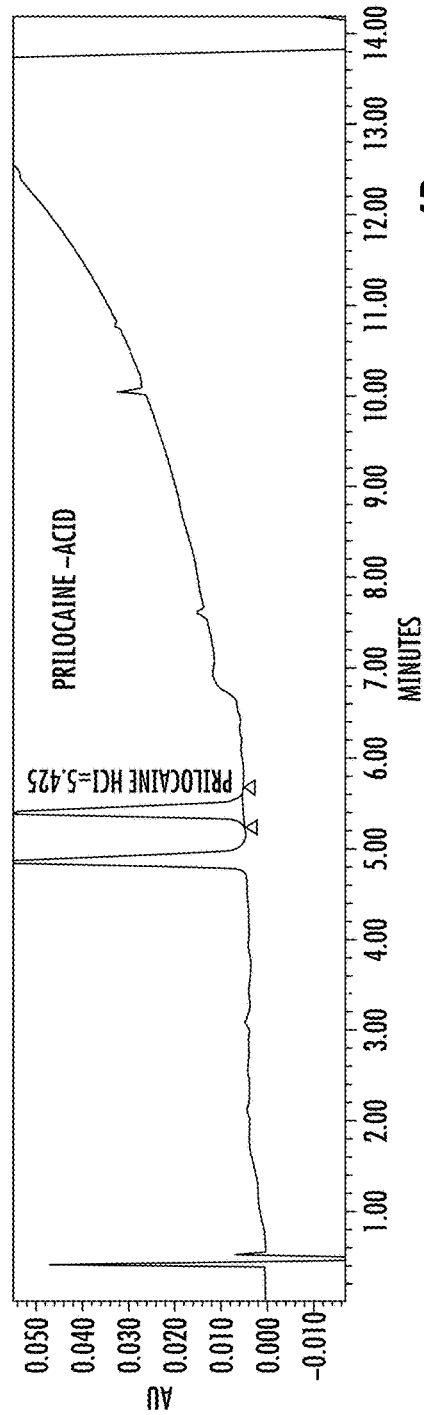
Figure 5A:
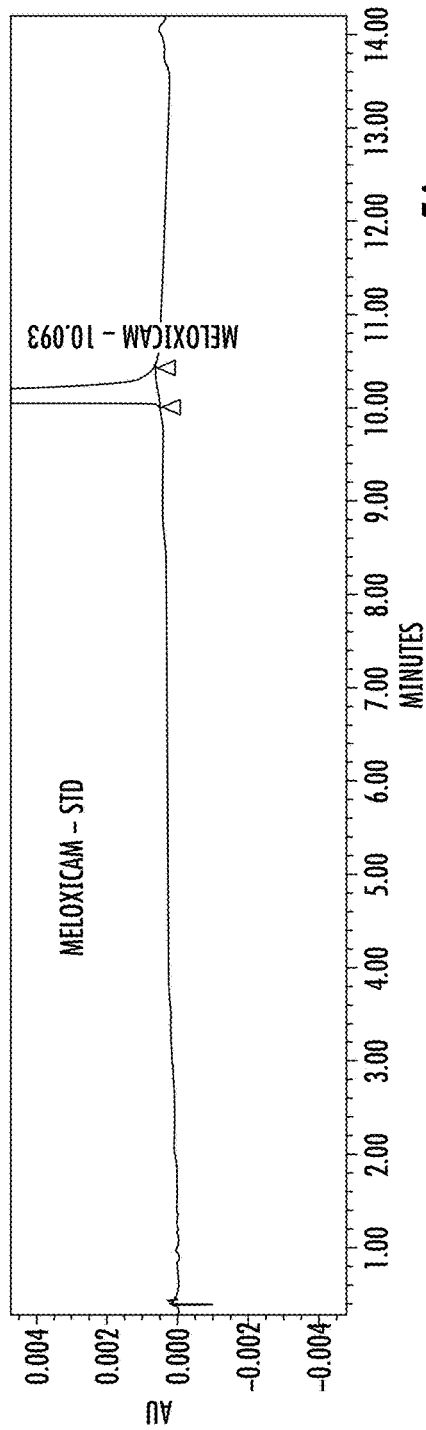
Figure 5B:
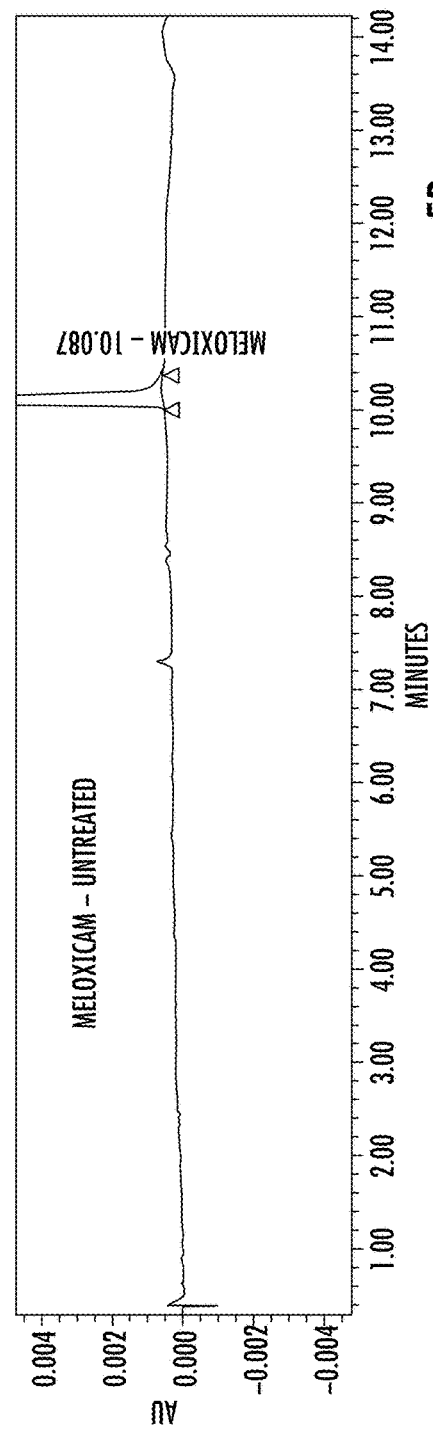

More specifically, FIG. 2 depicts an exemplary method of compounding medications with a transdermal cream 200. The method 200 depicted in FIG. 2 may be used to manufacture the transdermal creams discussed herein, including those discussed in relation to FIG. 1 above. The method 200 may include selecting a base composition 202; calculating an amount of active ingredients 204; grinding up the tablets containing the active ingredients 206; wetting the mixture with DMSO or Sterile Water for Irrigation 208; bringing to total weight 210; and milling in an ointment mill and mixing 212. The method 200 may include additional, fewer, or alternate actions.

The method 200 may include selecting a base composition 202 for a transdermal cream or gel. The base composition may include one or more local anesthetics, such as lidocaine and/or prilocaine. The base may include approximately equal amounts of lidocaine and prilocaine. The base composition may be a transdermal cream and may originally have approximately 2.5% lidocaine and approximately 2.5% prilocaine by weight. Other initial amounts of lidocaine and/or prilocaine may be used. In one embodiment, the base composition that includes lidocaine and/or prilocaine may be used in an amount of approximately 24,000 gm. Other amounts of base composition may be used.

The method 200 may include calculating an amount of active ingredients 204. The active ingredients may come in various size tablets. Noted herein, one of the transdermal cream embodiments, includes meloxicam and lamotrigine. For that embodiment, the ingredients may include 15 mg tablets of meloxicam, and approximately 1,500 of the 15 mg tables of meloxicam may be used. Tablets with other dosages of meloxicam may be used, and in different amounts. For instance, 7.5 mg or 30 mg tablets of meloxicam may be used.

The ingredients may also include 200 mg tablets of lamotrigine, and approximately 3,000 of the 200 mg tablets of lamotrigine may be used. Tablets with other dosages of lamotrigine may be used, and in different amounts. For instance, lamotrigine tablets ranging from 2 to 200 mg may be used.

To manufacture the transdermal cream embodiment that includes meloxicam and lamotrigine, the following formulas may be used to identify the amount of tablet powder of meloxicam and lamotrigine needed:

a. Meloxicam:
avg tab weight_____gm×tablets needed_____=tablet powder needed_____gm.

b. Lamotrigine:
avg tab weight_____gm×tablets needed_____=tablet powder needed_____gm.

The foregoing formulas may be used with the numbers stated above. For instance, the composition may require 1,500 of the 15 mg tables of meloxicam, and 3,000 of the 200 mg tablets of lamotrigine. As a result, in one embodiment, 22.5 grams of meloxicam and 600 grams of lamotrigine may be mixed with other ingredients, such as 24,000 gm of lidocaine 2.5%/prilocaine 2.5% cream, as well as 2,550 gm of dimethyl sulfoxide (DMSO). Instead of or in addition to lamotrigine, the medications added may include topiramate or other active ingredients. Instead of DMSO, Sterile Water for Irrigation may be used.

The method 200 may comprise grinding up the tablets containing the active ingredients 206. In one aspect, an automatic grinder may be used to grind up tablets containing one or more active ingredients into fine powder of medication. For instance, a Grindomix Mill may be used having a 100 volt, 60 Hz motor and five liter plastic container. The mill may have a standard lid, knife, and scraper. A five liter stainless steel container may be used that includes a knife holder. A knife of stainless steel may be used, and be autoclavable. The mill may have a plastic cover that is transparent.

The grinding up of the active ingredients into fine powder may allow for more precise amounts of each active ingredient in the final transdermal cream. This may be especially important when adding low amounts of active ingredients such that the final transdermal cream has low concentrations of various medications, which may reduce adverse allergic reactions to prolonged usage.

The method may include wetting the mixture with DMSO or Sterile Water for Irrigation 208. The DMSO and/or Sterile Water for Irrigation may facilitate the active ingredients penetrating the skin. After the ingredients in fine powder form are weighed, the preparer may triturate the powders of each ingredient together and wet with DMSO. For the 24,000 gm amount of lidocaine/prilocaine cream noted above, DMSO may be used in an amount of approximately 2,550 gm. Other amounts of DMSO may be used.

Instead of DMSO, the method may include wetting the mixture with only or primarily Sterile Water for Irrigation. Sterile Water for Irrigation USP may be a sterile, hypotonic, nonpyrogenic irrigating fluid or pharmaceutic aid (solvent), and may be composed of Sterile Water for Injection USP. It may be prepared by distillation and may contain no antimicrobial or bacteriostatic agents or added buffers. The pH may be about 5.7, or between 5.0 and 7.0. Sterile Water for Irrigation may be intended for use only as a single-dose, and may be classified as a sterile irrigant, wash, rinse, diluent and pharmaceutical vehicle. Instead of or addition to Sterile Water for Irrigation, Sterile Water for Injection or purified water may be used.

The method may include bringing to total weight with the lidocaine/prilocaine cream and mixing well 210. As noted elsewhere herein, after the fine powder of medication is mixed with the lidocaine/prilocaine base, the final transdermal cream may have approximately 2.0% by weight lidocaine, approximately 2.0% by weight prilocaine, approximately 0.09% by weight meloxicam, and approximately 2.5% by weight either lamotrigine or topiramate. The final transdermal cream may have other active ingredients as well, including those mentioned herein.

The method 200 may include milling the mixture in an ointment mill as necessary to acquire the desired consistency 212. After which, the preparer may mix the milled mixture thoroughly and package it in appropriate containers.

VI. Exemplary Storage Characteristics

The compounded transdermal creams discussed herein that are made using fine powder of medication may exhibit excellent storage characteristics, and avoid separation and/or degradation of the active ingredients from a base composition for substantial lengths of time, such as six months or greater. For example, Table I below depicts the results of a 198 day potency test for a transdermal cream including meloxicam, lamotrigine, lidocaine, and prilocaine. As shown, there is little degradation of the active ingredients. The sample was stored in approximately 20° C. to 25° C. (68° F. to 77° F.) conditions, and contained one large white tube with cream in a clear bag.

TABLE I

198 Day Potency Test

| Analyte/Specifications | Expected Amount | Units | Results | % of EXP. | Test Method |
|---|---|---|---|---|---|
| Lamotrigine Specifications = N/A | 2.5 | % | 2.463 | 98.5% | HPLC |
| Lidocaine Specifications = N/A | 2.0 | % | 1.927 | 96.4% | HPLC |
| Meloxicam Specifications = N/A | 0.09 | % | 0.0962 | 106.9% | HPLC |
| Prilocaine Specifications = N/A | 2.0 | % | 2.118 | 105.9% | HPLC |

Table II below depicts the results of a 100 day potency test for a transdermal cream including meloxicam, topiramate, lidocaine, and prilocaine. As shown, there is little degradation of the active ingredients. The sample was stored in approximately 20° C. to 25° C. (68° F. to 77° F.) conditions, and contained one large white tube with cream in a clear bag.

TABLE II

100 Day Potency Test

| Analyte/Specifications | Expected Amount | Units | Results | % of EXP. | Test Method |
|---|---|---|---|---|---|
| Lidocaine Specifications = N/A | 2.0 | % | 1.700 | 85.0% | HPLC |
| Meloxicam Specifications = N/A | 0.09 | % | 0.0945 | 105.0% | HPLC |
| Prilocaine Specifications = N/A | 2.0 | % | 1.899 | 95.0% | HPLC |
| Topiramate Specifications = N/A | 2.5 | % | 2.368 | 94.7% | HPLC |

VII. Exemplary Methods of Compounding Using Fine Powder

An exemplary method of compounding may include grinding up tablets of one or more active ingredients into a fine powder, and then adding those ingredients in powder form to a compounded transdermal cream or gel. The active ingredients that are ground up into a fine powder of medication may include one or more NSAIDs, anticonvulsants, nerve depressants, muscle relaxants, antidepressants, NMDA receptor antagonists, opioid or opiate agonists, local anesthetics, and/or other active agents. The transdermal cream or gel may or may not have one or more pre-existing ingredients prior to the addition of the fine powder of medication, such as one or more pre-existing local anesthetics.

The method may include grinding up tablets of one or more local anesthetics into a fine powder. The local anesthetics ground up into powder form may include lidocaine and/or prilocaine, or other agents. An amount of lidocaine and/or prilocaine powder may be added to the transdermal cream such that lidocaine comprises between approximately 0.5% and approximately 7.0% by weight of the transdermal cream, and that prilocaine comprises between approximately 0.5% and approximately 7.0% by weight of the transdermal cream. Other amounts may be used, including those discussed elsewhere herein.

The method may include grinding up tablets of one or more NSAIDs into a fine powder of medication. The NSAIDs that are ground up may include meloxicam, fluribiprofen, nabumetone, and/or other NSAIDs. The amount of NSAIDs may be between approximately 0.05% and 25.0% by weight of the transdermal cream. For instance, the transdermal cream may include meloxicam in a low amount of between approximately 0.05% and approximately 0.15% by weight of the transdermal cream, and/or flurbiprofen or nabumetone in an amount between approximately 5.0% and approximately 25.0% of the transdermal cream by weight. Other amounts may be used, including those discussed elsewhere herein.

The method may include grinding up tablets of one or more anticonvulsants into the fine powder of medication. The anticonvulsants that are ground up may include lamotrigine, topiramate, and/or other anticonvulsants. The transdermal cream may include an amount of anticonvulsant of between approximately 1.0% and approximately 5.0% by weight of the transdermal cream. Other amounts may be used, including those discussed elsewhere herein.

The method may include grinding up tablets of one or more muscle relaxants into a fine powder of medication. The muscle relaxants that are ground up may include baclofen, cyclobenzaprine, and/or other muscle relaxants. The transdermal cream may include an amount of muscle relaxant of between approximately 1.0% and approximately 5.0% by weight of the transdermal cream. Other amounts may be used, including those discussed elsewhere herein.

The method may include grinding up tablets of one or more opioid or opiate agonists into a fine powder of medication. The opioid or opiate agonists that are ground up may include C2 or C3 opiate agonists, tramadol, and/or others. The transdermal cream may include an amount of opioid or opiate agonist of between approximately 1.0% and approximately 5.0% by weight of the transdermal cream. Other amounts may be used, including those discussed elsewhere herein.

The method may include grinding up tablets of one or more NMDA receptor antagonists into a fine powder of medication. The NMDA receptor antagonists that are ground up may be ketamine and/or other antagonists. The transdermal cream may include an amount of NMDA receptor antagonist of between approximately 1.0% and approximately 40.0% by weight of the transdermal cream. Other amounts may be used, including those discussed elsewhere herein.

The method may include grinding up tablets of one or more nerve depressants into a fine powder of medication. The nerve depressants that are ground up may include gabapentin and/or other nerve depressants. The transdermal cream may include an amount of nerve depressant of between approximately 1.0% and approximately 15.0% by weight of the transdermal cream. Other amounts may be used, including those discussed elsewhere herein.

The method may include grinding up tablets of one or more tricyclic antidepressants or other antidepressants into a fine powder of medication. The tricyclic antidepressants that are ground up may include amitriptyline and/or other antidepressants. The transdermal cream may include an amount of antidepressant of between approximately 1.0% and approximately 15.0% by weight of the transdermal cream. Other amounts may be used, including those discussed elsewhere herein.

The fine powder of each active ingredient that is ground up may be added to a transdermal cream or gel separately or collectively. The medications may comprise approximately 20%, approximately 30%, or approximately 40% or more of a transdermal cream by weight. Other amounts may be used, including those discussed elsewhere herein. Alternatively, administering low doses or applying transdermal creams or gels with low concentrations of one or more active ingredients may minimize adverse side effects, such as adverse skin conditions that may develop with usage. Therefore, the method may include adding several medications in fine powder form to a transdermal cream or gel to alleviate the magnitude of any adverse skin conditions that may arise, while simultaneously providing a compounded therapy.

In specific embodiments, the two or more medications that are ground up into a fine powder may include (1) a NSAID (such as meloxicam) and an anticonvulsant (such as lamotrigine and/or topiramate); (2) a NSAID (such as fluribiprofen or nabumetone), a nerve depressant (such as gabapentin), and a muscle relaxant (such as baclofen or cyclobenzaprine); or (3) a NSAID (such as fluribiprofen or nabumetone), a nerve depressant (such as gabapentin), and an antidepressant (such as amitriptyline). Other combinations of medications may be used.

In one aspect, an amount of fine powder of several medications may be ground up and then added to a transdermal cream or gel. The several medications may include: (1) at least one local anesthetic, such as lidocaine and/or prilocaine, in an amount between approximately 1.0% and approximately 7.0% of the transdermal cream by weight; (2) at least one nerve depressant, such as gabapentin, in an amount between approximately 5.0% and approximately 15.0% of the transdermal cream by weight; (3) at least one NSAID, such as flurbiprofen or nabumetone, in an amount between approximately 5.0% and approximately 25.0% of the transdermal cream by weight; and/or (4) at least one muscle relaxant, such cyclobenzaprine, in an amount between approximately 0.5% and approximately 4.0% of the transdermal cream by weight such that multiple ailments may be addressed simultaneously. In one embodiment, the transdermal cream may comprise, by weight of the transdermal cream, approximately 2.0% lidocaine, approximately 2.0% prilocaine, approximately 6.0% gabapentin, approximately 1.0% cyclobenzaprine, and approximately 10.0% flurbiprofen or approximately 20% nabumetone. The several medications may also include an opioid or opiate agonist, a tricyclic or other antidepressant, a NMDA receptor antagonist, and/or other active ingredients.

In another aspect, an amount of fine powder of several medications may be ground up and then added to a transdermal cream or gel. The several medications may include: (1) at least one local anesthetic, such as lidocaine and/or prilocaine, in an amount between approximately 1.0% and approximately 7.0% of the transdermal cream by weight; (2) at least one nerve depressant, such as gabapentin, in an amount between approximately 5.0% and approximately 15.0% of the transdermal cream by weight; (3) at least one NSAID, such as flurbiprofen or nabumetone, in an amount between approximately 5.0% and approximately 25.0% of the transdermal cream by weight; and/or (4) at least one tricyclic antidepressant, such as amitriptyline, in an amount between approximately 0.5% and approximately 4.0% of the transdermal cream by weight. In one embodiment, the transdermal cream may comprise, by weight of the transdermal cream, approximately 2.0% lidocaine, approximately 2.0% prilocaine, approximately 6.0% gabapentin, approximately 1.0% amitriptyline, and approximately 10.0% flurbiprofen or approximately 20.0% nabumetone. The several medications may also include an opioid or opiate agonist, a muscle relaxant, a NMDA receptor antagonist, and/or other active ingredients.

In another aspect, an amount of fine powder of several medications may be ground up and then added to a transdermal cream or gel. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and lamotrigine and/or topiramate in an amount between approximately 0.5% and approximately 5.0% by weight of the transdermal cream. In one embodiment, the transdermal cream may comprise approximately 2.0% by weight of both lidocaine and prilocaine, approximately 0.09% by weight meloxicam, and approximately 2.5% by weight lamotrigine and/or topiramate. As a result, the transdermal cream or gel may allow for the topical administration of lidocaine, prilocaine, meloxicam, and lamotrigine and/or topiramate simultaneously during use. The several medications may also include an opioid or opiate agonist, a muscle relaxant, a NMDA receptor antagonist, a nerve depressant, other NSAIDs, other anticonvulsants, and/or other active agents, including those discussed elsewhere herein.

In another aspect, the transdermal cream comprises a nerve depressant, lidocaine, and prilocaine. A fine powder medication of one or more of the above medications may be obtained by crushing tablets of the medication, such as commercial tablets of the nerve depressant. In one such embodiment, the nerve depressant comprises or consists of gabapentin. In a further embodiment, the transdermal cream includes approximately 1% to approximately 10%, approximately 3% to approximately 9%, or approximately 5% to approximately 8% by weight gabapentin and approximately 0.5% to approximately 5.0% by weight of each of lidocaine and prilocaine with DMSO or without DMSO. In one such embodiment, the transdermal cream includes approximately 6% by weight gabapentin and approximately 2% by weight of each of lidocaine and prilocaine. In one embodiment of the above transdermal cream, the transdermal cream includes DMSO. In another embodiment, the transdermal cream does not include DMSO, e.g., DMSO-free.

In a further aspect, the transdermal cream may comprise a nerve depressant, lidocaine, prilocaine, and a NSAID. A fine powder medication of one or more of the above medications may be obtained by crushing tablets of the medication, such as commercial tablets of the nerve depressant and the NSAID. The fine powder medication may also be obtained from bulk sources, which may include powder medication that may be subsequently ground to fine powder or be provided in a fine powder form. In one particular instance of the above embodiment, the nerve depressant comprises or consists of gabapentin and the NSAID comprises or consists of diclofenac. In one embodiment, gabapentin and diclofenac are present in the transdermal cream in an amount approximately 1% to approximately 10%, approximately 1% to approximately 6%, or approximately 2% to approximately 5% by weight gabapentin, approximately 1% to approximately 10%, approximately 2% to approximately 8%, approximately 3% to approximately 7%, or approximately 4% to approximately 6% by weight diclofenac, and approximately 0.5% to approximately 5.0% by weight of each of lidocaine and prilocaine with DMSO or without DMSO. In one such embodiment, the transdermal cream includes approximately 3% by weight gabapentin, approximately 5% by weight diclofenac, and approximately 2% by weight of each of lidocaine and prilocaine. In one embodiment the transdermal cream includes DMSO. In another embodiment the transdermal cream does not include DMSO, e.g., DMSO-free.

In a further aspect, the transdermal cream may comprise a nerve depressant, an NSAID, lidocaine, prilocaine, and a muscle relaxant. A fine powder medication of one or more of the above active ingredients may be obtained by crushing tablets of the medication, such as commercial tablets of the nerve depressant, the NSAID, and the muscle relaxant. The fine powder medication may also be obtained from bulk sources, which may include powder medication that may be subsequently ground to fine powder or be provided in a fine powder form. In one particular instance of the above embodiment, the nerve depressant comprises or consists of gabapentin, the NSAID comprises or consists of diclofenac, and the muscle relaxant comprises cyclobenzaprine. In one embodiment, gabapentin, diclofenac, and cyclobenzaprine are present in the transdermal cream in an amount approximately 1% to approximately 10%, approximately 1% to approximately 6%, or approximately 2% to approximately 5% by weight gabapentin, approximately 1% to approximately 10%, approximately 2% to approximately 8%, approximately 3% to approximately 7%, or approximately 4% to approximately 6% by weight diclofenac, approximately 0.5% to approximately 2%, approximately 0.5% to approximately 1.5% by weight cyclobenzaprine, and approximately 0.5% to approximately 5.0% by weight of each of lidocaine and prilocaine with DMSO or without DMSO. In one such embodiment, the compounded transdermal cream includes approximately 3% by weight gabapentin, approximately 5% by weight diclofenac, approximately 1% by weight cyclobenzaprine, and approximately 2% by weight of each of lidocaine and prilocaine. In one embodiment the compounded transdermal cream includes DMSO. In another embodiment the compounded transdermal cream does not include DMSO, e.g., DMSO-free.

In one aspect, the compounded transdermal cream comprises a NSAID, lidocaine, and prilocaine. A fine powder medication of one or more of the above medications may be obtained by crushing tablets of the medication, such as commercial tablets of the NSAID. In one such embodiment, the NSAID is diclofenac. In a further embodiment, the compounded transdermal cream includes approximately 1% to approximately 10%, approximately 2% to approximately 8%, or approximately 4% to approximately 6% by weight of diclofenac and approximately 0.5% to approximately 5.0% by weight of each of lidocaine and prilocaine with DMSO or without DMSO. In one such embodiment, the compounded transdermal cream includes approximately 5% by weight of diclofenac and approximately 2% by weight of each of lidocaine and prilocaine. In one embodiment of the above transdermal cream, the transdermal cream comprising diclofenac includes DMSO. In another embodiment, the transdermal cream comprising diclofenac does not include DMSO, e.g., DMSO-free.

VIII. Exemplary Embodiments Methods of Compounding Using Solution

In one method of formulating a topically delivered compounded medication, one or more of the active ingredients are provided in an aqueous solution and combined with the base composition comprising lidocaine and prilocaine cream. The lidocaine and prilocaine cream preferably comprises an eutectic mixture of equal quantities (by weight) of lidocaine and prilocaine. The lidocaine and prilocaine cream may thus include an emulsifier. The lidocaine and prilocaine cream may further comprise lidocaine and prilocaine in an emulsion preparation wherein lidocaine and prilocaine are provided at a 1:1 ratio. Preferably the oil phase of the emulsion preparation comprises an eutectic mixture of lidocaine and prilocaine in a ratio of 1:1 by weight. For example, in one embodiment, the lidocaine and prilocaine cream comprises a 5% emulsion preparation, containing 2.5% each of lidocaine and prilocaine. In one embodiment, the lidocaine and prilocaine cream comprises an emulsifier comprising polyoxyethylene fatty acid esters. The lidocaine and prilocaine cream may further comprise a thickening agent. In one embodiment, the thickening agent comprises carboxypolymethylene. The lidocaine and prilocaine cream may further comprise additional excipients or inactive components such as sodium hydroxide and purified water.

In one embodiment, the method of formulating a topically delivered medication in which one or more active ingredients are provided in an aqueous solution and then combined and mixed with the base composition includes combining the aqueous solution and the base composition, wherein lidocaine and prilocaine are already in the cream, such as premixed or pre-incorporated into the cream. For example, the base composition may be a commercially manufactured lidocaine and prilocaine cream, such as lidocaine 2.5% and prilocaine 2.5% cream. In some such embodiments, a suitable lidocaine and prilocaine cream may be a lidocaine and prilocaine cream marketed under the trade name EMLA (Eutectic Mixture of Local Anesthetics) or a generic lidocaine and prilocaine cream, e.g., a lidocaine and prilocaine cream such as those manufactured by Hi-Tech Pharmacal Co., Inc., Amityville, N.Y., or E. Fougera & Co., a division of Fougera Pharmaceuticals Inc., Melville, N.Y. The above commercially manufactured lidocaine and prilocaine creams comprise a 5% emulsion preparation, containing approximately 2.5% of each of lidocaine and prilocaine. The lidocaine and prilocaine cream is provided in an emulsion in which the oil phase is a eutectic mixture of lidocaine and prilocaine present in a ratio of 1:1 by weight, having a melting point below room temperature, and, therefore, both local anesthetics exist as a liquid oil rather than as crystals at room temperature. Each gram of the lidocaine and prilocaine cream may contain lidocaine in an amount approximately 25 mg, prilocaine in an amount approximately 25 mg, polyoxyethylene fatty acid esters (as emulsifiers), carboxypolymethylene or carbomer 934 (as a thickening agent), sodium hydroxide, and purified water to 1 gram.

In various embodiments, the at least one active ingredient in aqueous solution may comprise an NSAID. As described above, the NSAID combined with the base composition may include one or more of: (1) oxicams—meloxicam and piroxicam; (2) salicylic acid derivatives—aspirin, diflunisal, salsalate, and trilisate; (3) propionic acids—flurbiprofen, ibuprofen, ketoprofen, naproxen, and oxaprozin; (4) acetic acids—diclofenac, etodolac, indomethacin, ketorolac, nabumetone, sulindac, and tolmetin; (5) fenamates—meclofenamate; and/or (6) COX-2 inhibitors—celecoxib, rofecoxib, and valdecoxib. In one embodiment, the NSAID comprises a benzeneacetic acid derivative such as diclofenac or pharmaceutically acceptable salt thereof provided in an aqueous solution. For example, the diclofenac may be provided in an aqueous solution comprising a diclofenac sodium solution. In one embodiment, the diclofenac or pharmaceutically acceptable salt thereof may comprise a diclofenac sodium solution for topical application. The diclofenac sodium solution may contain, for example, 1.5% (w/w) diclofenac sodium wherein each 1 mL of solution may contain approximately 16.05 mg of diclofenac sodium. In one embodiment, the diclofenac solution comprises a diclofenac sodium solution 1.5% (w/w) such as that manufactured under the trade name PENNSAID® by Nuvo Manufacturing, Varennes, Quebec, Canada for treating the pain of osteoarthritis of the knee. The diclofenac solution may also contain various inactive ingredients such as dimethyl sulfoxide USP (DMSO, 45.5% w/w), ethanol, glycerin, propylene glycol and purified water. In one embodiment, the diclofenac solution comprises a diclofenac sodium solution marketed under the trade name PENNSAID® and manufactured by Nuvo Manufacturing, Varennes, Quebec, Canada, in a 2% (w/w) diclofenac solution for treating the pain of osteoarthritis of the knee. Each gram of solution may contain approximately 20 mg of diclofenac sodium and various inactive ingredients such as dimethyl sulfoxide USP (DMSO, 45.5% w/w), ethanol, purified water, propylene glycol, and hydroxypropyl cellulose. In other embodiments, other concentrations of diclofenac solution, such as diclofenac sodium solutions, may be used.

The compounded transdermal cream formulated by combining a commercial NSAID solution such as diclofenac sodium solution with lidocaine and prilocaine cream according to the embodiments described herein possess surprising stability. For example, formulations wherein components comprise a solution and a carboxy polymer cream base often times will "crack". The compounded transdermal cream, however, has been found to be incredibly stable and pristine in appearance. In various embodiments, DMSO makes up approximately 45.5% of the diclofenac solution (1.5% Stock Solution) and comprises approximately 10% of the final finished compound, and the final compound may have approximately 5% DMSO in it.

The combined diclofenac solution and lidocaine and prilocaine cream may be milled, e.g., in an ointment mill, and blended to achieve a desired creamy consistency wherein the active ingredients are approximately evenly dispersed within the compounded transdermal cream.

The compounded transdermal cream formulated by combining a commercially manufactured lidocaine and prilocaine cream and a commercially manufactured diclofenac sodium solution such as a diclofenac sodium may comprise relatively low concentrations of the active ingredients compared to conventional topical formulations including one or more of the active ingredients. Due to the formulation and combination described herein, the present compounded transdermal cream may provide similar effectiveness while having an increased safety profile. The increased safety profile may be especially beneficial to patients with gastric bleeds, on blood thinners, etc. The compounded composition may also provide local anesthetics benefits while promoting deeper penetration into the skin and leveraging DMSO in the diclofenac sodium solution that would be embedded into the compounded transdermal cream.

In a one embodiment, a method of formulating a compounded medication product comprises combining a commercially manufactured lidocaine 2.5% and prilocaine 2.5% cream and a commercially manufactured diclofenac sodium solution such as a diclofenac sodium 1.5% (w/w) or diclofenac sodium 2.0% (w/w) solution to form a compounded transdermal cream whereby the final concentration by weight of the compounded transdermal cream comprises diclofenac or diclofenac sodium at a concentration of approximately 0.1% to approximately 1.0%, lidocaine at a concentration of approximately 1.5% to approximately 2.25%, and prilocaine at a concentration of approximately 1.5% to approximately 2.25%. In further embodiments, the method of formulating a compounded drug product comprises combining a commercially manufactured lidocaine 2.5% and prilocaine 2.5% cream and a commercially manufactured diclofenac solution such as a diclofenac sodium 1.5% (w/w) or diclofenac sodium 2.0% (w/w) solution whereby the final concentration by weight of the compounded drug product comprises diclofenac or diclofenac sodium at a concentration of approximately 0.1% to approximately 0.1% to approximately 0.75%, approximately 0.1% to approximately 0.5%, approximately 0.1% to approximately 0.3%, approximately 0.2% to approximately 0.75%, approximately 0.2% to approximately 0.5%, approximately 0.2% to approximately 0.3%, approximately 0.3% to approximately 0.75%, approximately 0.3% to approximately 0.5%, or approximately 0.5% to approximately 0.75%, lidocaine at a concentration of approximately 1.5% to approximately 2.25%, and prilocaine at a concentration of approximately 1.5% to approximately 2.25%. In further embodiments, the method may also include combining one or more additional active ingredient medications comprising one or more additional NSAIDs, one or more additional local anesthetics, one or more anticonvulsants, one or more nerve depressants, one or more muscle relaxants, one or more antidepressants, one or more NMDA receptor antagonists, or one or more opioid or opiate agonists, and/or other active agents.

The one or more additional NSAIDs that may be further added to or included in the compounded transdermal cream, e.g., combined with the lidocaine and prilocaine cream or the diclofenac sodium solution prior to combining the lidocaine and prilocaine cream and the diclofenac sodium solution or to the compounded transdermal cream comprising the combined diclofenac sodium solution and the lidocaine and prilocaine cream, may be present in an amount between approximately 0.1% and approximately 5.0% by weight of the final compounded transdermal cream and selected from salicylic acid derivatives selected from aspirin, diflunisal, salsalate, and trilisate; propionic acids selected from flurbiprofen, ibuprofen, ketoprofen, naproxen, and oxaprozin; tolmetin; eclofenamate; COX-2 inhibitors selected from celecoxib, rofecoxib, and valdecoxib, oxicams selected from meloxicam, piroxicam; or an additional acetic acid selected from etodolac, indomethacin, ketorolac, nabumetone, and sulindac. The one or more anticonvulsants selected from lamotrigine or topiramate may be added to or included in the compounded transdermal cream, e.g., combined with the lidocaine and prilocaine cream or the diclofenac sodium solution prior to combining the lidocaine and prilocaine cream and the diclofenac sodium solution or to the compounded transdermal cream comprising the combined diclofenac sodium solution and the lidocaine and prilocaine cream, in an amount between approximately 0.1% and approximately 5.0% of the total weight of the final compounded transdermal cream. The one or more nerve depressants may include gabapentin added to or included in the compounded transdermal cream comprising diclofenac, lidocaine, and prilocaine in an amount between approximately 0.1% and approximately 5.0% of the total weight of the final compounded transdermal cream. The one or more muscle relaxants that may be added to or included in the compounded transdermal cream comprising diclofenac, lidocaine, and prilocaine may be provided in an amount between approximately 0.1% and approximately 5.0% of the total weight of the final compounded transdermal cream, wherein the one or more muscle relaxants are selected from baclofen, carisoprodol, chlorzoxazone, cyclobenzaprine, dantrolene, diazepam, metaxalone, methocarbamol, orphenadrine, quinine sulfate, tizanidine, and/or other muscle relaxants. The one or more NMDA receptor antagonists may include ketamine added to or included in the compounded transdermal cream comprising diclofenac, lidocaine, and prilocaine in an amount between approximately 0.1% and approximately 5.0% of the total weight of the final compounded transdermal cream.

In various embodiments, all or a portion of the one or more additional active ingredient medications may comprise a fine powder obtained by grinding commercial tablets of the active ingredient. In some such embodiments or other embodiments, all or a portion of the one or more additional active ingredients may comprise a fine powder obtained from a bulk powder source. The one or more additional active ingredient medications may be dissolved or suspended in a solution or suspension or provided in a solution or suspension and subsequently combined with the lidocaine and prilocaine cream before, after, or along with, e.g., combined with, the diclofenac sodium solution.

In one particular embodiment, one or more additional active ingredients are provided in the form of a fine dry powder obtained from a bulk source, crushed commercial tablets, or both, as described herein, may be dissolved or suspended in a diclofenac sodium 1.5% (w/w) or 2.0% (w/w) solution and then combined with the lidocaine 2.5% and prilocaine 2.5% cream to form the compounded transdermal cream for topical administration. In a one embodiment, one or more additional active ingredients are provided in the form of a fine dry powder obtained from a bulk source, crushed commercial tablets, or both, as described herein, may be combined with the lidocaine and prilocaine 2.5% cream until moistened after which diclofenac sodium 1.5% (w/w) or 2.0% (w/w) solution may be added to form the compounded transdermal cream for topical administration.

A method of compounding the transdermal cream may comprise combining diclofenac sodium solution, fine powder of one or more active ingredient medications obtained from crushed tablets of one or more nerve depressants and/or anticonvulsants, and a lidocaine and prilocaine cream. In one formulation, the one or more anticonvulsants are selected from lamotrigine, topiramate, or a combination thereof and may be added to or included in the compounded transdermal cream, e.g., combined with the lidocaine and prilocaine cream or the diclofenac sodium solution prior to combining the lidocaine and prilocaine cream and the diclofenac sodium solution or to the compounded transdermal cream comprising the diclofenac sodium solution combined with the lidocaine and prilocaine cream, in an amount between approximately 0.1% and approximately 5.0% of the total weight of the final compounded transdermal cream. The one or more nerve depressants may include gabapentin added to or included in the compounded transdermal cream comprising diclofenac, lidocaine, and prilocaine in an amount between approximately 0.1% and approximately 5.0% of the total weight of the final compounded transdermal cream. In one embodiment, diclofenac sodium solution Diclofenac sodium 1.5% (w/w) or diclofenac sodium 2.0% (w/w) solution, the fine powder obtained from crushed tablets of one or more nerve depressants and/or anticonvulsants selected from gabapentin, topiramate, lamotrigine, or combination thereof, and a lidocaine and prilocaine cream, such as a commercially manufactured lidocaine 2.5% and prilocaine 2.5% cream, may be combined to produce the compounded transdermal cream. The fine powder of medication may be combined such that medication introduced from the fine powder is present in the compounded transdermal cream in an amount between approximately 0.1% and 5.00% by weight.

In various embodiments, the diclofenac sodium solution may contain DMSO. For example, DMSO may make up approximately 45.5% of the diclofenac solution (1.5% Stock Solution). The finished compounded transdermal cream may comprise approximately 10% diclofenac sodium 1.5% (w/w) solution and approximately 5% DMSO. Diclofenac sodium 1.5% (w/w) or diclofenac sodium 2.0% (w/w) solution may be added to obtain a concentration by weight of diclofenac or diclofenac sodium in the compounded drug product of approximately 0.05% to approximately 0.25%, approximately 0.05% to approximately 0.2%, approximately 0.05% to approximately 0.15%, approximately 0.1% to approximately 0.15%, approximately 0.12% to approximately 0.15%, or approximately 0.15%. According to one method of making a compounded drug product comprising a transdermal cream having approximately 0.15% diclofenac or diclofenac sodium, approximately 0.1 gm or approximately 0.0935 mL diclofenac sodium 1.5% (w/w) solution may be added per gram of final compounded drug product. The diclofenac sodium solution may be added to the lidocaine and prilocaine cream before, after, or with the fine powder composition. For example, the fine powder may be wetted, dissolved, or suspending in the diclofenac sodium solution and then added to the cream. The diclofenac sodium solution may be added in whole or in part to the cream and the fine powder may be added to the mixture of diclofenac sodium solution and cream. The diclofenac sodium solution may be added in whole or in part to the cream having the fine powder moistened or mixed therein.

The fine powder of medication that includes one or more antidepressants and/or anticonvulsants obtained from ground tablets of medication may include an anticonvulsant in a low amount between approximately 0.1% and approximately 5.0% by weight of the final compounded transdermal cream. In one embodiment, the final compounded transdermal cream comprises approximately 2.5% of lamotrigine, topiramate, or a combination thereof, by weight. Other amounts may be used, including those discussed elsewhere herein. In one embodiment, a fine powder of lamotrigine, topiramate, or combination thereof may be added to a achieve a concentration in the final compounded transdermal cream of approximately 1.0% to approximately 4.0%, approximately 1.0% to approximately 3.0%, approximately 1.0% to approximately 2.5%, approximately 1.5% to approximately 3.0%, approximately 1.5% to approximately 2.5%, approximately 1.5% to approximately 2.5%, or approximately 2.0% to approximately 2.5%. Topiramate tablets for oral administration are produced in various strengths such as 25 mg, 50 mg, 100 mg, and 200 mg strengths. The tablets typically contain additional inactives, which may include candelilla wax, croscarmellose sodium, hypromellose, lactose monohydrate, magnesium stearate, microcrystalline cellulose, macrogol, polyethylene glycol, polysorbate 80, pregelatinised starch, sodium starch glycolate, and titanium dioxide. Colorants may include iron oxides. In one example formulation comprising 2.5% topiramate, each gram of the compounded transdermal cream may include approximately 0.125 tablets of 200 mg topiramate tablets; however, other tablet strengths may be used wherein the amount of topiramate tablet(s) is modified to account for strength difference. The 200 mg topiramate tablets may have an average weight of approximately 0.654 g per tablet. The 200 mg topiramate tablets may be ground to a fine powder. The fine powder may be added in an amount of approximately 0.08175 gm per gram of the final compounded transdermal cream to obtain approximately 25 mg/g or approximately 2.5% topiramate in the final compounded transdermal cream. Lamotrigine tablets for oral administration are produced in various strengths such as 25 mg, 100 mg, 150 mg, and 200 mg strengths. The tablets typically contain additional inactives, which may include colloidal silicon dioxide, lactose monohydrate, magnesium stearate, microcrystalline cellulose, povidone, pregelatinized starch, and sodium starch glycolate. Additional colorants may include FD&C Yellow #6, ferric oxide yellow, and FD&C Blue #2. In one example formulation comprising 2.5% lamotrigine, each gram of the compounded transdermal cream may include approximately 0.125 tablets of 200 mg lamotrigine tablets ground to a fine powder. The amount of fine powder added to obtain approximately 25 mg or 0.025 gm lamotrigine per gram of the final transdermal cream or approximately 2.5% lamotrigine in the final compounded transdermal cream may be determined by multiplying the portion of the tablet providing 25 mg lamotrigine by the weight of the tablet and the final desired weight of the compounded transdermal cream. The proportion of the table providing 25 mg lamotrigine may be determined by dividing 25 mg by the strength of the tablet, 200 mg in this example.

The nerve depressant may be added such that the amount of nerve depressant in the transdermal cream may be between approximately 0.1% and approximately 5.0% of the total weight of the transdermal cream. The nerve depressant may be added in addition to or instead of one or more anticonvulsants. Nerve depressants that may be added may include gabapentin and/or others. Commercially available gabapentin tablets for oral administration include 300 mg, 600 mg, and 800 mg strengths. The tablets typically contain additional inactives, which may include candelilla wax, copolyvidonum, cornstarch, hydroxypropyl cellulose, magnesium stearate, poloxamer 407, and talc. In one embodiment, a fine powder of gabapentin obtained from crushed commercial tablets may be combined with the diclofenac sodium solution and lidocaine and prilocaine cream in an amount sufficient to achieve a concentration of approximately 1.0% to approximately 4.0%, approximately 1.0% to approximately 3.0%, approximately 1.0% to approximately 2.5%, approximately 1.5% to approximately 3.0%, approximately 1.5% to approximately 2.5%, approximately 1.5% to approximately 2.5%, or approximately 2.0% to approximately 2.5% of gabapentin by weight of the final compounded transdermal cream. The gabapentin may be combined with the diclofenac sodium solution and lidocaine and prilocaine cream instead of or in addition to, e.g., in combination with, one or both lamotrigine and topiramate.

The lidocaine and prilocaine cream may be combined in an amount sufficient to provide the final compounded transdermal cream with approximately 1.0% to approximately 5.0%, approximately 1.0% to approximately 4.0%, approximately 1.0% to approximately 3.0%, approximately 1.0% to approximately 2.5%, approximately 1.5% to approximately 3.0%, approximately 1.5% to approximately 2.5%, approximately 1.5% to approximately 2.0%, approximately 1.75% to approximately 2.25%, or approximately 2.0% of each of lidocaine and prilocaine by weight. According to one method of compounding the transdermal cream, the lidocaine and prilocaine cream is a commercially available lidocaine 2.5% and prilocaine 2.5% cream. According to one method of compounded the transdermal cream where the cream comprises approximately 2% of each of lidocaine and prilocaine by weight, 0.8183 gm of lidocaine 2.5% and prilocaine 2.5% cream is added per gram of the final compounded transdermal cream.

An exemplary method of compounding the transdermal cream according to various embodiments described here may comprise grinding tablets comprising the active ingredient medications having nerve depressant activity, such as a nerve depressant, anticonvulsant, or combinations thereof, into a fine powder. A mixing container containing the lidocaine and prilocaine cream may be positioned onto a lift in a powder containment hood and raised into the protected area. Diclofenac sodium solution and the fine powder may be added to the cream in the mixing container. The fine powder may be moistened with the cream to ensure that that dry particles are not dispersed into the surrounding environment during mixing. The mixing container containing the mixture may be transferred to a mixer and mixed for approximately 15 minutes on low. The mixture may then be milled in an ointment mill for approximately an additional 15 minutes on low. The ointment mill may be an Exakt 120S-450 Three Roll Mill, front roller "1", rear roller "3". The compounded transdermal cream may then be packaged in appropriate tubes.

An exemplary method of compounding the transdermal cream according to various embodiments described here may comprise grinding respective tablets comprising the active ingredient medications having NSAID activity and nerve depressant activity, such as a nerve depressant, anticonvulsant, or combinations thereof, into a fine powder. The fine powder of medications may be added to the cream base, e.g., lidocaine and prilocaine cream. The resulting transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and gabapentin in an amount between approximately 0.5% and approximately 5.0% by weight of the transdermal cream. When the cream base is lidocaine and prilocaine cream, the resulting transdermal cream will have less than 2.5% by weight of each of lidocaine and prilocaine unless mixture is supplemented with additional lidocaine or prilocaine, e.g., in powder or liquid solution form.

In one embodiment, a method of compounding a transdermal cream comprising approximately 2.0%, such as approximately 2.15%, by weight of both lidocaine and prilocaine, approximately 0.09% by weight meloxicam, and approximately 2.5% by weight gabapentin may include crushing tablets of meloxicam and gabapentin to form a fine powder and adding the fine powder to lidocaine and prilocaine cream. Each gram of compounded transdermal cream includes fine powder from 0.0625 25 mg meloxicam tablets having an average weight of 0.179 g per tablet. Each gram of compounded transdermal cream includes fine powder from 0.0313 800 mg gabapentin tablets having an average tablet weight of 1.11 g per tablet. The fine powder may be added to the lidocaine and prilocaine cream (2.5%/2.5%), wherein each gram of the compounded transdermal cream contains approximately 0.86 g of lidocaine and prilocaine cream. Additional powders, excipients, base creams, wetting agents, etc. may be added to desired weight. For example, for every gram of compounded transdermal cream, approximately 0.0941 grams of liquid may be added, which, in some embodiments, may be used as a wetting agent. The liquid may comprise those described herein, e.g., DMSO, water, purified water, water for injection, etc. In a further embodiment, the fine powder may be added to approximately 0.954 gm of lidocaine and prilocaine cream resulting in a compounded transdermal cream comprising approximately 2.385% by weight of each of lidocaine and prilocaine.

IX. Additional Exemplary Embodiments

The present embodiments may include the presence of DMSO and/or Sterile Water for Irrigation, such as DMSO or Sterile Water for Irrigation in a sufficient quantity to allow for the topical delivery of the active ingredients mentioned herein. For instance, during the methods discussed herein, the DMSO may be removed and replaced with Sterile Water for Irrigation. The transdermal cream may be DMSO-free. The transdermal cream of the present embodiments may be compounded to have no bulk ingredients in it. For example, one or more of the ingredients may be obtained from crushing tablets comprising the ingredients. The tablets may comprise commercially manufactured tablets formulated for oral administration. The tablets may therefore further include various excipients formulated for oral administration, which may include gastrointestinal, sublingual, buccal, or other suitable route of oral administration. According to some embodiments, the transdermal cream of the present embodiments may be compounded with one or more, including, in at least one embodiment, all ingredients obtained through bulk sources. The bulk sources may comprising one or more of the ingredients in a powder, such as a fine powder form.

In one aspect, compounded meloxicam, topiramate (and/or lamotrigine), lidocaine, and prilocaine cream may contain strictly commercially available medications. DMSO, which may be in some cream embodiments disclosed herein, may be replaced with Sterile Water for Irrigation. Sterile Water for Irrigation may act as a primary or sole penetration enhancer in some embodiments.

Although experimentation and investigation continues, it is believed that some detriments may develop from a transition to a DMSO-free compounded transdermal cream. It is believed that the removal of DMSO from certain compounds may decrease the effectiveness of the compound given that the primary penetrant is no longer present. Also, patients that have received the previous compounded version containing DMSO may experience lower efficacy rates. It is also believed that the transition of the formula may, at best, give the same efficacy that the patients previously had experienced, and, at worst, decrease efficacy due to the absence of DMSO.

On the other hand, the use of Sterile Water for Irrigation instead of DMSO may be cheaper and involve an easier method of manufacture. Also, Sterile Water for Irrigation is an FDA-approved commercially available medication.

In one embodiment, the transdermal cream comprises a nerve depressant, lidocaine, and prilocaine. A method of compounding the transdermal cream may comprise adding the fine powder medication comprising the nerve depressant to a starting transdermal cream or base. As described above, the fine powder medication may be obtained by crushing tablets of the medication, such as commercial tablets of the nerve depressant. As also described above, the fine powder medication may be obtained using bulk sources, which may include powder that may be ground to fine powder or the medication in a fine powder form. The fine powder of medication, e.g., nerve depressant, may be added to a transdermal cream or base composition containing both lidocaine and prilocaine. In another embodiment, the fine powder medication added to the transdermal cream or base composition further includes one or both lidocaine and prilocaine. In one particular instance of the above embodiment, the nerve depressant comprises or consists of gabapentin. In a further embodiment, gabapentin is added to the starting transdermal cream or base composition in a sufficient amount such that the final transdermal cream includes the approximately 1% to approximately 10%, approximately 3% to approximately 9%, or approximately 5% to approximately 8% by weight gabapentin and approximately 0.5% to approximately 5.0% by weight of each of lidocaine and prilocaine with DMSO or without DMSO. In one such embodiment gabapentin is added to the starting transdermal cream or base composition in a sufficient amount such that the final transdermal cream includes the approximately 6% by weight gabapentin and approximately 2% by weight of each of lidocaine and prilocaine. In one embodiment the final transdermal cream includes DMSO. In another embodiment the final transdermal cream does not include DMSO. For example, the method of compounding the above transdermal cream may include addition of DMSO to the starting transdermal cream or base or to the cream or base after gabapentin has been added or at an intermediate point of the compounding process. As described herein, all or a portion of the fine powder medication may be wetted with DMSO prior to addition to the transdermal cream. In embodiments without DMSO, the fine powder medication may be added directly to the cream or base or, in some embodiments, the fine powder medication may be wetted with liquid such as Sterile Water for Irrigation.

In a further embodiment, the transdermal cream comprises a nerve depressant, lidocaine, prilocaine, and a NSAID. The method of compounding the transdermal cream may further comprise adding the fine powder medication comprising the nerve depressant and NSAID to a starting transdermal cream or base. The fine powder medication comprising the fine powders of the nerve depressant and NSAID may be added together or separate. As described above, the fine powder medication may be obtained by crushing tablets of the medication, such as commercial tablets of the nerve depressant and the NSAID. As also described above, the fine powder medication may be obtained from bulk sources, which may include powder medication that may be ground to fine powder or the medication in a fine powder form. The fine powder medication, e.g., a nerve depressant and NSAID, may be added to the transdermal cream or base composition containing both lidocaine and prilocaine, which may be a commercially manufactured lidocaine and prilocaine cream, such as lidocaine 2.5% and prilocaine 2.5% cream. In another embodiment, the fine powder medication added to the transdermal cream or base composition further includes one or both lidocaine and prilocaine. In one particular instance of the above embodiment, the nerve depressant comprises or consists of gabapentin and the NSAID comprises or consists of diclofenac. In one embodiment, gabapentin and diclofenac are added to the starting transdermal cream or base composition in a sufficient amount such that the final transdermal cream includes approximately 1% to approximately 10%, approximately 1% to approximately 6%, or approximately 2% to approximately 5% by weight gabapentin, approximately 1% to approximately 10%, approximately 2% to approximately 8%, approximately 3% to approximately 7%, or approximately 4% to approximately 6% by weight diclofenac, and approximately 0.5% to approximately 5.0% by weight of each of lidocaine and prilocaine with DMSO or without DMSO. In one such embodiment gabapentin and diclofenac are added to the starting transdermal cream or base composition in sufficient amounts such that the final transdermal cream includes the approximately 3% by weight gabapentin, approximately 5% by weight diclofenac, and approximately 2% by weight of each of lidocaine and prilocaine. In one embodiment the final transdermal cream includes DMSO. In another embodiment the final transdermal cream does not include DMSO. For example, the method of compounding the above transdermal cream may include addition of DMSO to the starting transdermal cream or base or to the cream or base after gabapentin, diclofenac, or both have been added or at an intermediate point of the compounding process. As described herein, all or a portion of the fine powder medication may be wetted with DMSO prior to addition to the starting transdermal cream or base composition. In embodiments without DMSO, the fine powder medication may be added directly to the cream or base or, in some embodiments, the fine powder medication may be wetted with liquid such as Sterile Water for Irrigation.

In additional embodiments, the compounded transdermal cream comprises a nerve depressant, NSAID, lidocaine, prilocaine, and a muscle relaxant. The method of compounding the transdermal cream may further comprise adding the fine powder medication comprising the nerve depressant, NSAID, and muscle relaxant to a starting transdermal cream or base. The fine powder medication comprising the fine powders of the nerve depressant, NSAID, and muscle relaxant may be added together or separate. As described above, the fine powder medication may be obtained by crushing tablets of the medication, such as commercial tablets of the nerve depressant, the NSAID, the muscle relaxant. As also described above, the fine powder medication may be obtained from bulk sources, which may include powder medication that may be ground to fine powder or the medication in a fine powder form. The fine powder medication, e.g., the nerve depressant, the NSAID, and the muscle relaxant, may be added to the transdermal cream or base composition containing both lidocaine and prilocaine. In another embodiment, the fine powder medication added to the transdermal cream or base composition further includes one or both lidocaine and prilocaine, which may be a commercially manufactured lidocaine and prilocaine cream, such as lidocaine 2.5% and prilocaine 2.5% cream. In one particular form of the above embodiment, the nerve depressant comprises or consists of gabapentin, the NSAID comprises or consists of diclofenac, and the muscle relaxant comprises or consists of cyclobenzaprine. In one embodiment, gabapentin, diclofenac, and cyclobenzaprine are added to the starting transdermal cream or base composition in a sufficient amount such that the final transdermal cream includes the approximately 1% to approximately 10%, approximately 1% to approximately 6%, or approximately 2% to approximately 5% by weight gabapentin, approximately 1% to approximately 10%, approximately 2% to approximately 8%, approximately 3% to approximately 7%, or approximately 4% to approximately 6% by weight diclofenac, approximately 0.5% to approximately 1.5% by weight cyclobenzaprine and approximately 0.5% to approximately 5.0% by weight of each of lidocaine and prilocaine with DMSO or without DMSO. In one such embodiment gabapentin and diclofenac are added to the starting transdermal cream or base composition in sufficient amounts such that the final transdermal cream includes the approximately 3% by weight gabapentin, approximately 5% by weight diclofenac, approximately 1% by weight cyclobenzaprine, and approximately 2% by weight of each of lidocaine and prilocaine. In one embodiment the final transdermal cream includes DMSO. In another embodiment the final transdermal cream does not include DMSO. For example, the method of compounding the above transdermal cream may include addition of DMSO to the starting transdermal cream or base or to the cream or base after gabapentin, diclofenac, or both have been added or at an intermediate point of the compounding process. As described herein, all or a portion of the fine powder medication may be wetted with DMSO prior to addition to the starting transdermal cream or base composition. In embodiments without DMSO, the fine powder medication may be added directly to the cream or base or, in some embodiments, the fine powder medication may be wetted with liquid such as Sterile Water for Irrigation.

In one embodiment, the transdermal cream comprises a NSAID, lidocaine, and prilocaine. A method of compounding the transdermal cream may comprise adding the fine powder medication comprising the NSAID to a starting transdermal cream or base. As described above, the fine powder medication may be obtained by crushing tablets of the medication, such as commercial tablets of the NSAID. As also described above, the fine powder medication may be obtained using bulk sources, which may include powder that may be ground to fine powder or the medication in a fine powder form. The fine powder of medication, e.g., NSAID, may be added to a transdermal cream or base composition containing both lidocaine and prilocaine, which may be a commercially manufactured lidocaine and prilocaine cream, such as lidocaine 2.5% and prilocaine 2.5% cream. In another embodiment, the fine powder medication added to the transdermal cream or base composition further includes only one lidocaine and prilocaine. In one particular instance of the above embodiment, the NSAID comprises or consists of diclofenac. In a further embodiment, diclofenac is added to the starting transdermal cream or base composition in a sufficient amount such that the final transdermal cream includes the approximately 1% to approximately 10%, approximately 2% to approximately 8%, or approximately 4% to approximately 6% by weight of diclofenac and approximately 0.5% to approximately 5.0% by weight of each of lidocaine and prilocaine with DMSO or without DMSO. In one such embodiment either the diclofenac or the ibuprofen is added to the starting transdermal cream or base composition in a sufficient amount such that the final compounded transdermal cream includes the approximately 5% by weight diclofenac and approximately 2% by weight of each of lidocaine and prilocaine. In one embodiment the final compounded transdermal cream includes approximately 5% by weight diclofenac and DMSO. In another embodiment the final compounded transdermal cream does not include DMSO. For example, the method of compounding the above transdermal cream may include addition of DMSO to the starting transdermal cream or base or to the cream or base after diclofenac has been added or at an intermediate point of the compounding process. As described herein, all or a portion of the fine powder medication, for example, the diclofenac, may be wetted with DMSO prior to addition to the transdermal cream. In embodiments without DMSO, the fine powder medication, for example, the ibuprofen, may be added directly to the cream or base or, in some embodiments, the fine powder medication, for example, the ibuprofen, may be wetted with liquid such as Sterile Water for Irrigation.

In one aspect, a transdermal cream that permits the simultaneous administration of multiple medications in low concentrations may be provided. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and lamotrigine in an amount between approximately 0.5% and approximately 5.0% by weight of the transdermal cream. In one embodiment, the transdermal cream may comprise approximately 2.0% by weight of both lidocaine and prilocaine, approximately 0.09% by weight meloxicam, and approximately 2.5% by weight lamotrigine. As a result, the transdermal cream may allow for the topical administration of lidocaine, prilocaine, meloxicam, and lamotrigine simultaneously during use. The transdermal cream may further include only or primarily Sterile Water for Irrigation as a penetration enhancer or other component, and be devoid of DMSO or DMSO-free.

In another aspect, a transdermal cream that permits the simultaneous administration of multiple medications in low concentrations may be provided. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and topiramate in an amount between approximately 0.5% and approximately 5.0% by weight of the transdermal cream. In one embodiment, the transdermal cream may comprise approximately 2.0% by weight of both lidocaine and prilocaine, approximately 0.09% by weight meloxicam, and approximately 2.5% by weight topiramate. As a result, the transdermal cream may allow for the topical administration of lidocaine, prilocaine, meloxicam, and topiramate simultaneously during use. The transdermal cream may further include only or primarily Sterile Water for Irrigation for penetration enhancement or as a wetting component, and/or be devoid of DMSO or DMSO-free.

In another aspect, a transdermal cream that permits the simultaneous administration of multiple medications in low concentrations may be provided. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and gabapentin in an amount between approximately 0.5% and approximately 5.0% by weight of the transdermal cream. In one embodiment, the transdermal cream may comprise approximately 2.0%, such as approximately 2.15%, by weight of both lidocaine and prilocaine, approximately 0.09% by weight meloxicam, and approximately 2.5% by weight gabapentin. As a result, the transdermal cream may allow for the topical administration of lidocaine, prilocaine, meloxicam, and gabapentin simultaneously during use. The transdermal cream may further include only or primarily Sterile Water for Irrigation for penetration enhancement or as a wetting component, and/or be devoid of DMSO or DMSO-free.

In another aspect, a method of compounding one or more medications with a transdermal cream for the topical administration of a compounded therapy may be provided. The method may include grinding up one or more tablets of a NSAID, an anticonvulsant, a nerve depressant, a muscle relaxant, a NMDA (N-Methyl-D-aspartate) receptor antagonist, an opiate or opioid agonist, and/or antidepressant into a fine powder of medication. In an alternate aspect, one or more, including all, of the medications may be obtained from bulk sources. The medications obtained from bulk sources may be in the form of a powder, which may be a fine powder or may be further ground into a fine powder prior to compounding with the transdermal cream or gel, which may be a commercially manufactured lidocaine and prilocaine cream, such as lidocaine 2.5% and prilocaine 2.5% cream. The method may include wetting the fine powder of medication mixture with DMSO or Sterile Water for Irrigation. The method may also include adding the fine powder of medication to a transdermal cream or base composition containing both lidocaine and prilocaine, the transdermal cream including both lidocaine and prilocaine in an amount of between approximately 0.5% and approximately 7.0% by weight of the transdermal cream, respectively. The method may include adding the fine powder of compounded medication to the starting transdermal cream or base composition in a sufficient amount such that the final transdermal cream includes the compounded medication that is ground up in a low amount of between approximately 0.01% and approximately 5.0% by weight of the transdermal cream. In one embodiment, an amount of ground up medication is added to the base composition such that the final transdermal cream contains low concentrations of several active ingredients and is approximately 2.0% by weight lidocaine, approximately 2.0% by weight prilocaine, approximately 0.09% by weight meloxicam, and approximately 2.5% by weight either lamotrigine or topiramate. As noted above, method may include mixing medications with the base composition for topical administration to a patient. The medications may include one or more local anesthetics, such as lidocaine, prilocaine, or benzocaine; one or more NSAIDs, such as meloxicam; and one or more nerve depressants and/or anticonvulsants, such as gabapentin, topiramate, or lamotrigine. Accordingly, the method may include addition of a fine powder of gabapentin in addition to or instead of topiramate or lamotrigine. Thus, in one embodiment, the method may include adding the fine powder of compounded medication to the starting transdermal cream or base composition in a sufficient amount such that the final transdermal cream includes the compounded medication that is ground up in a low amount of between approximately 0.01% and approximately 5.0% by weight of the transdermal cream. In one embodiment, an amount of ground up medication is added to the base composition such that the final transdermal cream contains low concentrations of several active ingredients and is approximately 2.0% by weight lidocaine, approximately 2.0% by weight prilocaine, approximately 0.09% by weight meloxicam, and approximately 2.5% by weight gabapentin. In one embodiment, the transdermal cream may further include only or primarily Sterile Water for Irrigation for penetration enhancement or as a wetting component, and/or be devoid of DMSO or DMSO-free.

In another aspect, a method of compounding medications with a transdermal cream for the topical administration of a compounded therapy may be provided. The method may include grinding up tablets of two or more medications into a fine powder of compounded medication. The two or more compounded medications to be ground up may be selected from a NSAID, an anticonvulsant, a nerve depressant, a muscle relaxant, a NMDA receptor antagonist, a local anesthetic, an antidepressant, and an opioid or opiate agonist. The method may include wetting the fine powder of compounded medication with DMSO or Sterile Water for Irrigation. The method may include then adding the fine powder of compounded medication to a transdermal cream or gel such that the transdermal cream or gel allows for topical delivery of the two or more compounded medications for simultaneous treatment of two or more ailments when the transdermal cream or gel is topically applied. The transdermal cream may further include only or primarily Sterile Water for Irrigation for penetration enhancement or as a wetting component, and/or be devoid of DMSO or other penetration enhancers.

The present disclosure also includes a stability-indicating method for the analysis of compounded transdermal creams. As presented in the following example forced degradation study performed on a compounded transdermal cream preparation comprising Meloxicam/Gabapentin/Lidocaine/Prilocaine Cream 0.09%/2.5%/2.15%/2.15%, the methods used are stability-indicating. The methods described below and similar may be used to establish stability-indicating methods for analysis of other compounded transdermal creams using similarly designed forced degradation studies.

At least two degradation conditions may be used to determine specificity. In the exemplary protocol, two degradation conditions, heat and acid, were used. With respect to the heat degradation condition, 1 gram samplings of the preparation were heated at 40° C., 65° C., and 80° C. At day 2, day 3, day 5 and day 16, the treated samples were taken out and analyzed. With respect to the acid degradation condition, 120 uL of 0.1N HCl was added to 1 gram samplings of the preparation. The acid degradation treated samplings were then either kept at room temperature or heated at 40° C. and 65° C. At day 2, day 3, day 5 and day 16, the treated samplings were taken out and analyzed. Samples were prepared by addition of 24 ml of Methanol to 1 gram of preparation. Each sample was then vortexed for 1 minute, microwaved twice for 5 seconds, sonicated for 2 minutes, vortexed for 1 minute, and centrifuged for 15 minutes. The extract was injected directly for the analysis of Meloxicam. A 1:10 dilution with Methanol was done for the analysis of Lidocaine and Prilocaine. For the analysis of Gabapentin, the extract was further diluted with DI Water to 5 ug/mL. An internal standard was added to obtain a same final concentration. Samplings of the heat and acid treated preparations were treated the same way. Lidocaine standard was prepared by accurately weighing and dissolving Lidocaine Hydrochloride USP Monohydrate (PCCA, C169931) in Methanol to a final concentration of 110 to 130 µg/mL. Prilocaine standard was prepared by accurately weighing and dissolving Prilocaine Hydrochloride USP (PCCA, C171202) in Methanol to a similar final concentration. Meloxicam standard was prepared by accurately weighing and dissolving Meloxicam USP (PCCA, C168649) in Methanol to a concentration of 100 pg/mL. Gabapentin standard was prepared with Gabapentin USP (PCCA, C162777) in DI water as well as the internal standard (S)-(+)-a-Aminocyclohexanepropionic acid hydrate (Sigma, lot# MKBP4348V).

Standards and samples for Lidocaine, Prilocaine, and Meloxicam were analyzed with a gradient method on a Waters Acquity UPLC equipped with a PDA detector. Eluent A was prepared by adding 1 mL of Trifluroacetic acid to 1 L of DI Water. Eluent B was prepared by adding 1 mL of Trifluoroacetic acid to 1 L of Acetonitrile. The flow rate was 1 mL per minute. The column temperature was 50° C. The injection volume was 2 uL. The sample tray was kept at 22° C. The LC column was Acclaim RSLC PA2 Polar Advantage II, 2.2 um 120 A 2.1×150 mm from Thermo Scientific. The analysis time was 14 minutes with an additional 1 minute delay. The gradient was set as described in Table III. The processing wavelengths were 215 nm for Lidocaine, 220 nm for Prilocaine and 353 nm for Meloxicam.

TABLE III

Gradient Used for Analysis of Standards and Samples of Lidocaine, Prilocaine, Meloxicam

| Minutes | Eluent A % | Fluent B % |
|---|---|---|
| 0 | 98.0 | 2.0 |
| 6 | 88.0 | 12.0 |
| 13 | 20.0 | 80.0 |
| 13.2 | 98.0 | 2.0 |

Standards and samples for Gabapentin were analyzed with a gradient method on a Waters Acquity UPLC equipped with a PDA detector as well as a QDa detector. Eluent A was prepared by adding 1 mL of Formic acid to 1 L of DI Water. Eluent B was prepared by adding 1 mL of Formic acid to 1 L of Acetonitrile. The flow rate was 0.8 mL per minute. The column temperature was 50° C. The injection volume was 1 uL. The sample tray was kept at 22° C. The UPLC column was Acquity UPLC BEH C18 1.7 um 2.1×50 mm from Waters. The analysis time was 2.1 minutes with an additional 1 minute delay. The gradient was set as described in Table IV. The QDa detector was operated in the positive scan mode; the cone voltage was set at 15 V; the capillary voltage was set at 0.8 kV; the ions were scanned from 50 to 600 Daltons to obtain a total ion chromatogram. Standards and samples were monitored at (M+H)+=172.24 Daltons for Single Ion Monitoring (SIM).

TABLE IV

Gradient Used for Analysis of Standards and Samples of Meloxicam

| Minutes | Eluent A % | Eluent B % |
|---|---|---|
| 0 | 95.0 | 5.0 |
| 1.50 | 40.0 | 60.0 |
| 2.00 | 5.0 | 95.0 |
| 2.10 | 95.0 | 5.0 |

Percent recoveries of Lidocaine for untreated and treated samples are shown in Table V. FIGS. 3A-3D present exemplary chromatograms of standard, untreated, heat treated, and acid treated Lidocaine samples, respectively. Retention time for Lidocaine is at 4.89 minutes.

TABLE V

Recovery of Lidocaine (%)

| | Day 0 | Day 2 | Day 3 | Day 5 |
|---|---|---|---|---|
| Untreated | 102 | 106 | 99.0 | 103 |
| 40° C. | | 102 | 99.0 | 96.7 |
| 65° C. | | 94.1 | 86.1 | 86.4 |
| 80° C. | | 70.0 | 58 | 49.9 |
| H+, RT | | 104 | 101 | 102 |
| H+, 40° C. | | 100 | 96.8 | 99.4 |
| H+, 65° C. | | 93.8 | 85.6 | 83.8 |

RT = 22-25° C.

Percent recoveries of Prilocaine for untreated and treated samples are shown in Table VI. FIGS. 4A-4D present exemplary chromatograms of standard, untreated, heat treated, and acid treated Prilocaine samples, respectively. Retention time for Prilocaine is at 5.34 minutes.

TABLE VI

Recovery of Prilocaine (%)

| | Day 0 | Day 2 | Day 3 | Day 5 |
|---|---|---|---|---|
| Untreated | 101 | 101 | 102 | 99.0 |
| 40° C. | | 98.7 | 96.4 | 92.9 |
| 65° C. | | 90.0 | 87.7 | 83.2 |
| 80° C. | | 60.7 | 48.3 | 40.7 |
| H+, RT | | 98.2 | 96.5 | 97.2 |
| H+, 40° C. | | 96.4 | 92.6 | 93.2 |
| H+, 65° C. | | 90.6 | 51.3 | 81.9 |

RT = 22-25° C.

Percent recoveries of Meloxicam for untreated and treated samples are shown in Table VII. FIGS. 5A-5D present exemplary chromatograms of standard, untreated, heat treated, and acid treated Meloxicam samples, respectively. Retention for Meloxicam is at 10.9 minutes. The acid degradation of Meloxicam shows a degradant peak at 10.404 minutes.

TABLE VII

Recovery of Meloxicam (%)

| | Day 0 | Day 2 | Day 3 | Day 5 | Day 16 |
|---|---|---|---|---|---|
| Untreated | 102 | 104 | 102 | 103 | 102 |
| 40° C. | | 101 | 102 | 102 | 102 |
| 65° C. | | 101 | 101 | 100 | 95.5 |
| 80° C. | | 95.9 | 93.3 | 90.3 | 52.0 |
| H+, RT | | 103 | 101 | 101 | 101 |
| H+, 40° C. | | 102 | 101 | 102 | 100 |
| H+, 65° C. | | 101 | 99.5 | 97.7 | 89.3 |

RT = 22-25° C.

Figure 6A:
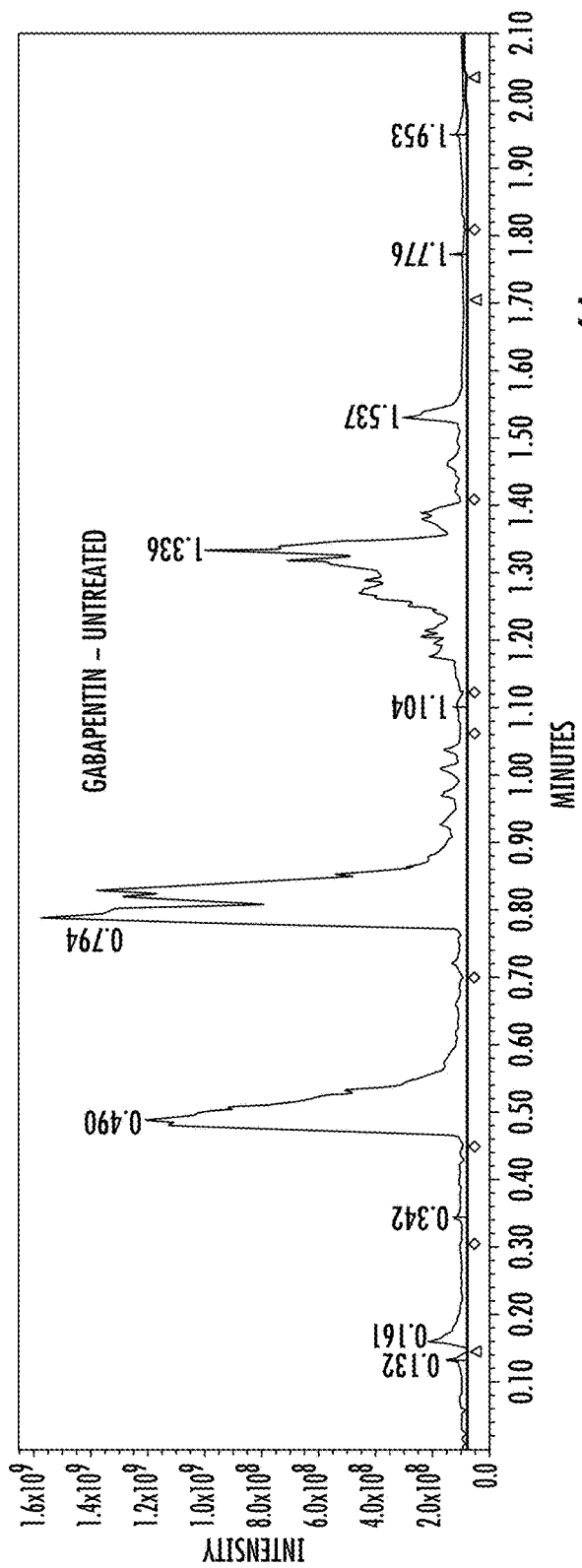
FIGS. 6A-6C present exemplary Total Ion Chromatograms (TIC) for the untreated, heat treated, and acid treated Gabapentin samples, respectively, generated in a degradation study according to various embodiments described herein.
Figure 6B:
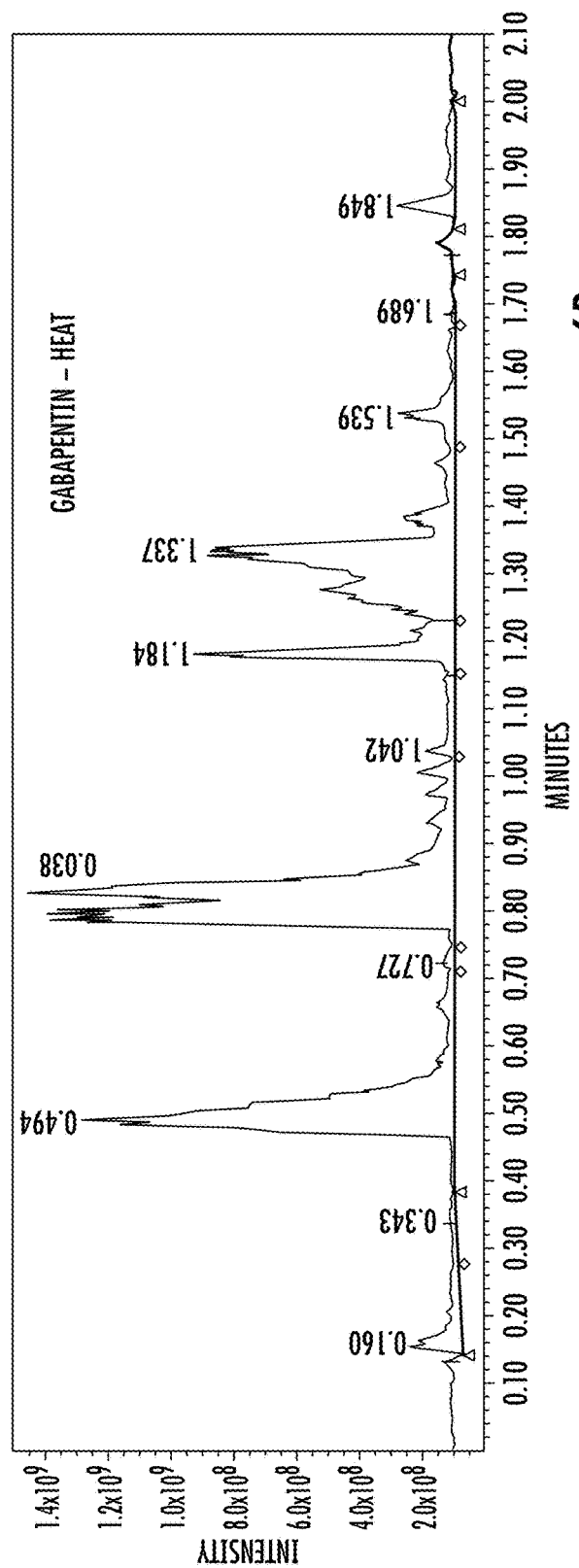
Figure 6C:
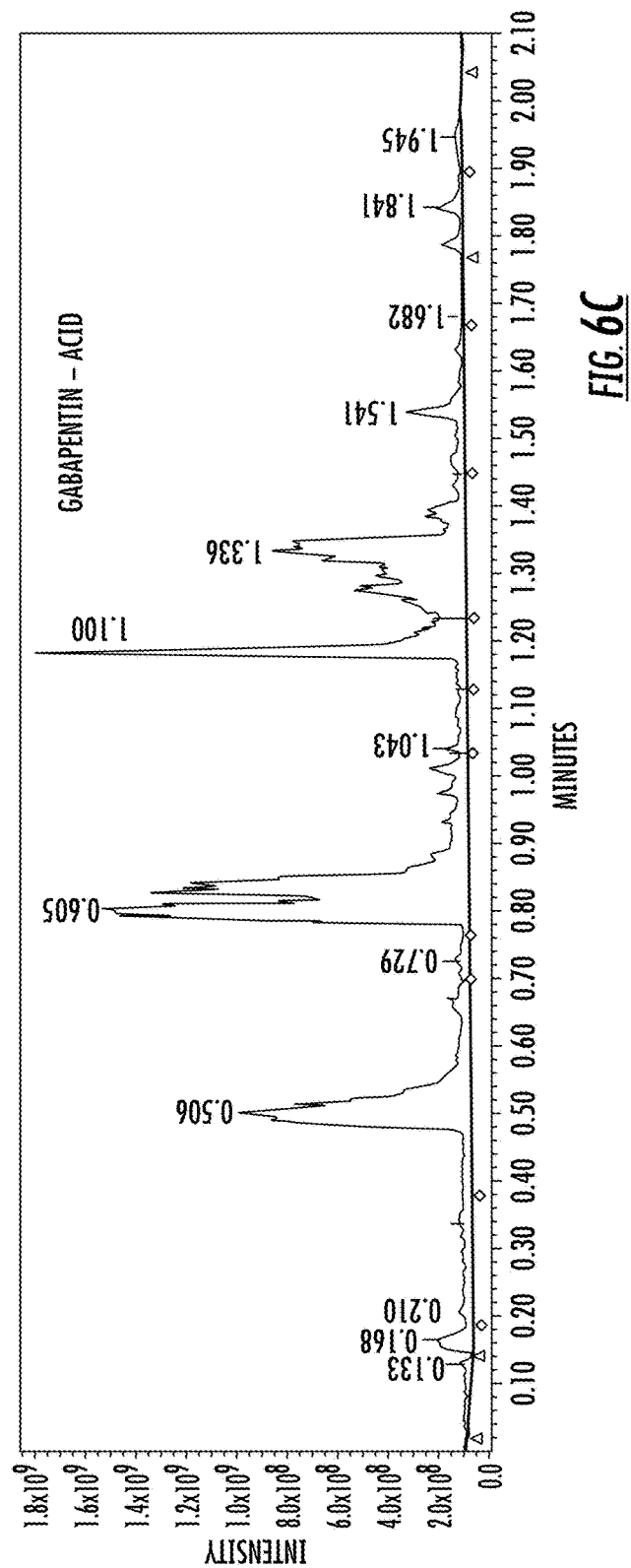
Figure 7A:
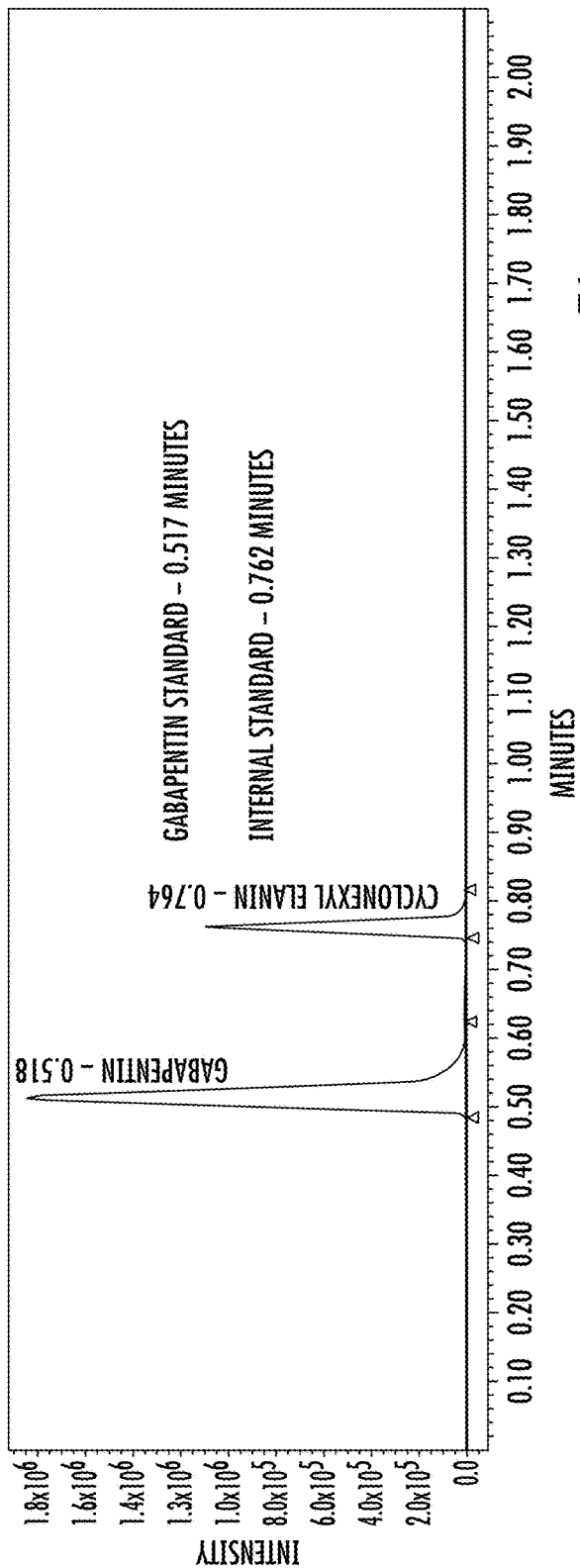
FIGS. 7A-7D present exemplary chromatograms showing the standard, untreated, heat treated, and acid treated gabapentin samples, respectively, generated in a Single Ion Monitoring (SIM) experiment of a degradation study according to various embodiments described herein.
Figure 7B:
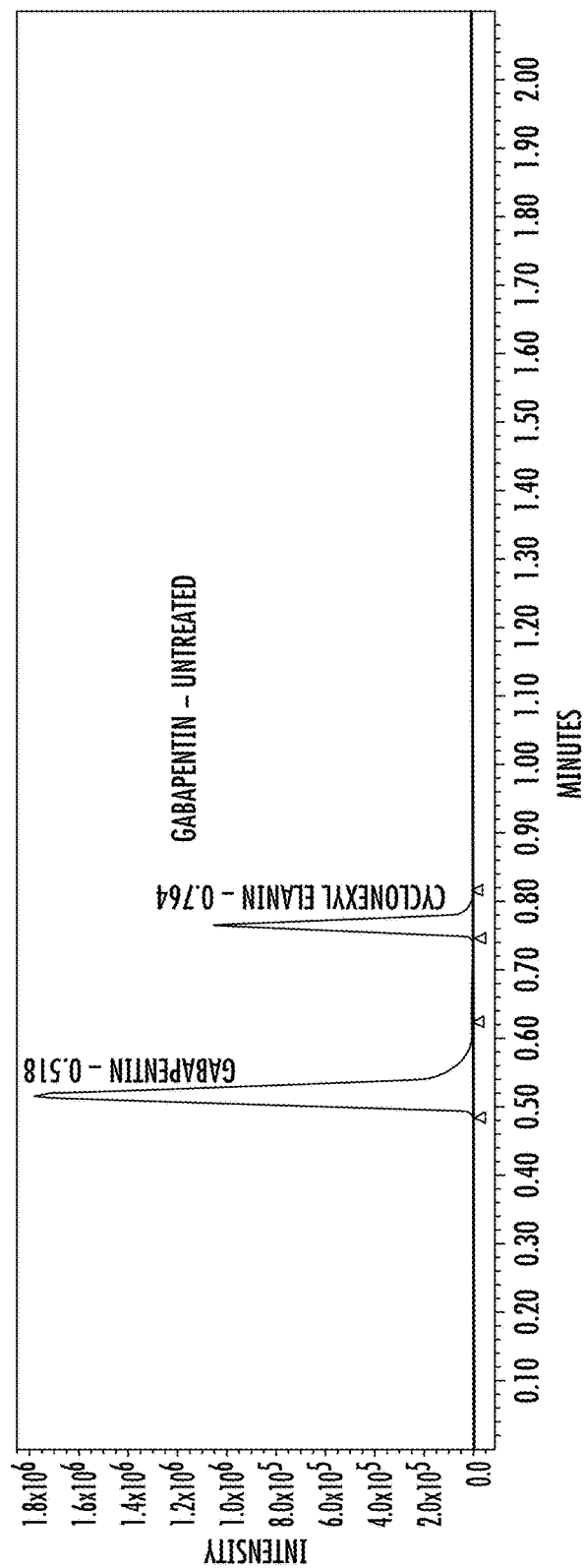
Figure 7C:
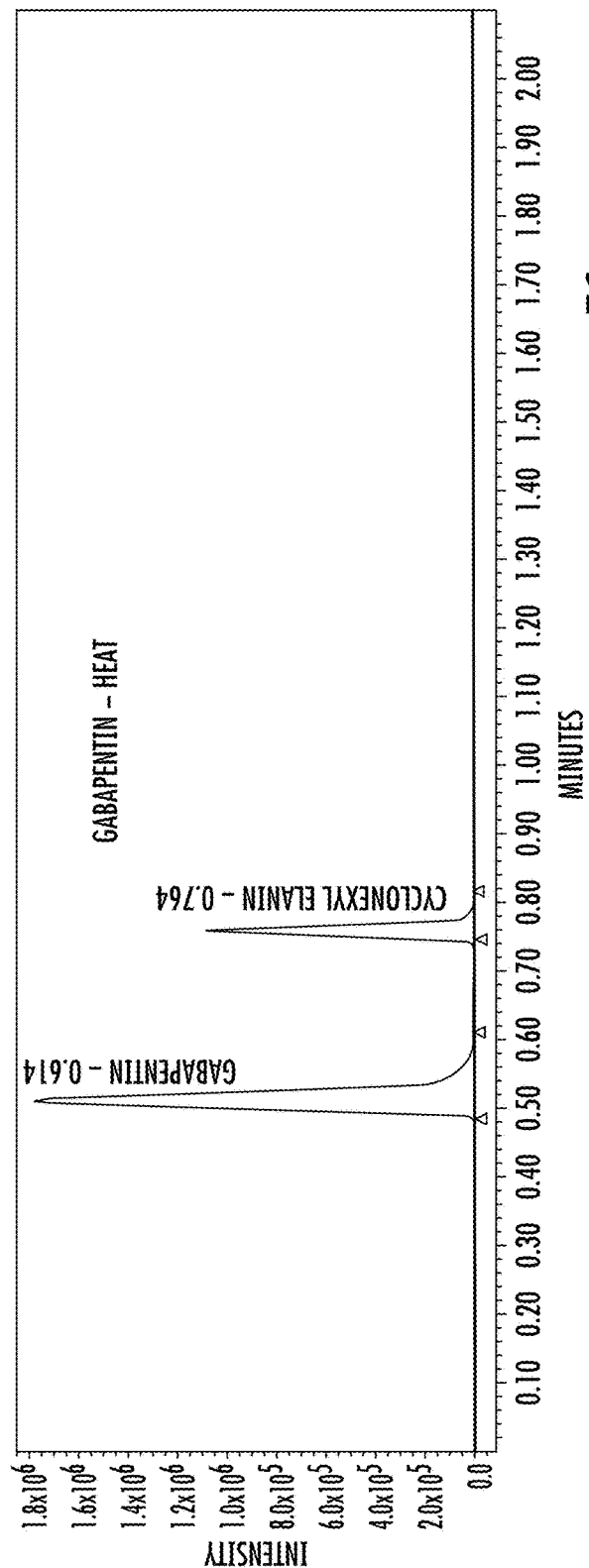
Figure 7D:
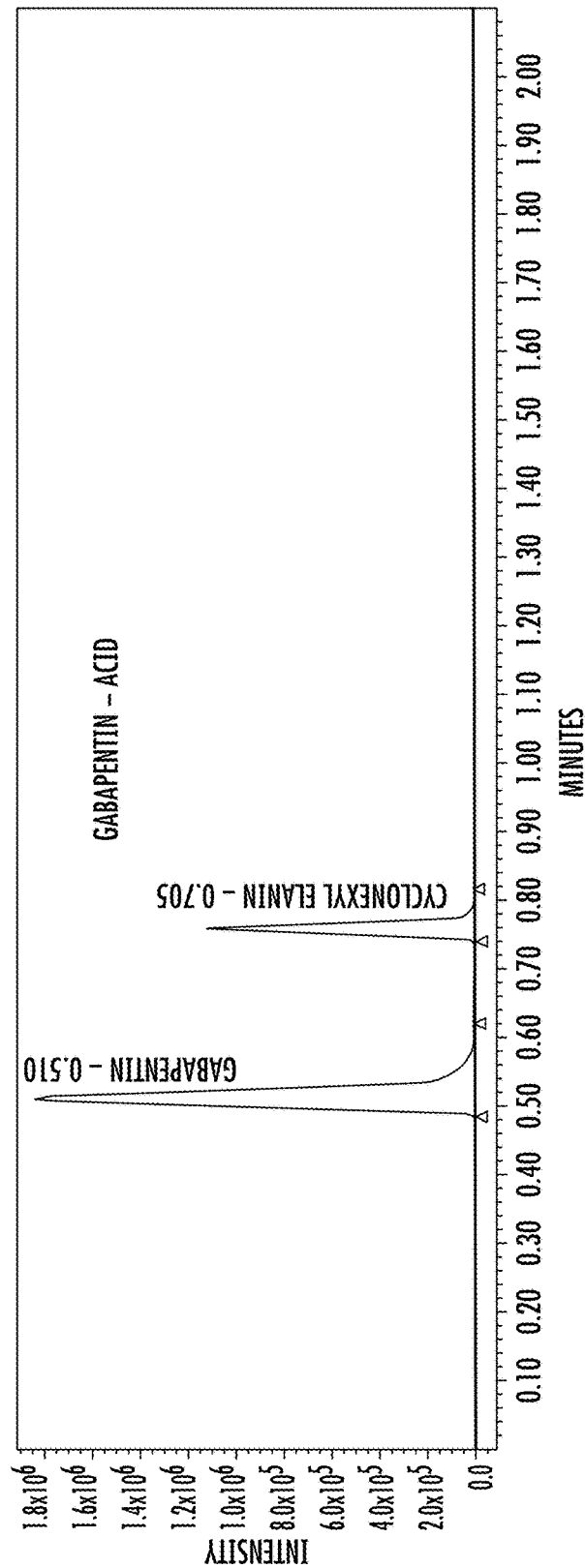

The Total Ion Chromatograms (TIC) are shown in FIGS. 6A-6C present exemplary Total Ion Chromatograms (TIC) for the untreated, heat treated, and acid treated Gabapentin samples, respectively. As a high concentration was needed for this TIC experiment, samples were not diluted. The extracts were injected directly and did not contain the internal standard. The retention time of Gabapentin was at 0.49 minute. The major degradant at 1.18 minute was caused both by acid and by heat.

FIGS. 7A-7D present exemplary chromatograms showing the standard, untreated, heat treated, and acid treated gabapentin samples for the SIM experiment. The retention time of the internal standard would be at 0.72 minutes. At that retention time, (M+H)*172.24 was not seen. This indicated that no interference between the internal standard and the degradation products.

The above degradation study performed for Lidocaine, Prilocaine, Meloxicam and Gabapentin in Meloxicam/Gabapentin/Lidocaine/Prilocaine 0.09%/2.5%/2.15%/2.15 Cream shows no co-elution or interference between degradants and API in all samples (stressed and untreated), thus, it demonstrates specificity. The methods used for this study are therefore stability-indicating methods.

The present invention may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

What is claimed is:

1. A method of making a compounded transdermal cream, the method comprising: grinding up one or more tablets of a Non-Steroidal Anti-Inflammatory Drug (NSAID) to produce a fine powder, wherein the NSAID comprises meloxicam; grinding up one or more tablets of one or more nerve depressants to produce a fine powder, wherein the one or more nerve depressants comprises gabapentin; wetting the ground fine powders with a wetting agent; and adding the wetted ground fine powders to an eutectic mixture of lidocaine and prilocaine in an emulsified topical cream in the form of a lidocaine 2.5%-prilocaine 2.5% cream to form a compounded transdermal cream, wherein the compounded transdermal cream comprises between 0.05% and 0.15% by weight meloxicam, between 1.0% and 5.0% by weight gabapentin, and 80% or more by weight of the eutectic mixture comprising lidocaine and prilocaine in an emulsified topical cream in the form of a lidocaine 2.5%-prilocaine 2.5% cream, and wherein the percent weights of lidocaine and prilocaine are in matched amounts.

2. The method of claim 1, wherein the compounded transdermal cream comprises 0.09% by weight meloxicam.

3. The method of claim 2, wherein the compounded transdermal cream comprises 2.15% by weight of each of lidocaine and prilocaine.

4. The method of claim 1, wherein the compounded transdermal cream comprises 2.5% by weight gabapentin.

5. The method of claim 4, wherein the compounded transdermal cream comprises 2.15% by weight of each of lidocaine and prilocaine.

6. The method of claim 1, wherein the compounded transdermal cream comprises 0.09% by weight meloxicam and 2.5% by weight gabapentin.

7. The method of claim 6, wherein the compounded transdermal cream comprises 2.15% by weight of each of lidocaine and prilocaine.

8. The method of claim 7, wherein the wetting agent comprises purified water.

* * * * *